US007902161B2

(12) United States Patent
Kwon et al.

(10) Patent No.: US 7,902,161 B2
(45) Date of Patent: Mar. 8, 2011

(54) **OLIGONUCLEOTIDES DERIVED FROM *MYCOBACTERIUM* FOR STIMULATING IMMUNE FUNCTION, TREATING IMMUNE-RELATED DISEASES, ATOPIC DERMATITIS AND/OR PROTECTING NORMAL IMMUNE CELL**

(75) Inventors: Hyung-Joo Kwon, Cheongju-si (KR); Tae-Yoon Kim, Seoul (KR); Doo-Sik Kim, Seoul (KR)

(73) Assignees: Hyung-Joo Kwon, Chungcheongbuk-do (KR); Tae-Yoon Kim, Seoul (KR)

( * ) Notice: Subject to any disclaimer, the term of this patent is extended or adjusted under 35 U.S.C. 154(b) by 191 days.

(21) Appl. No.: 10/581,656

(22) PCT Filed: Jan. 28, 2005

(86) PCT No.: PCT/KR2005/000266
§ 371 (c)(1),
(2), (4) Date: Jun. 9, 2008

(87) PCT Pub. No.: WO2006/080596
PCT Pub. Date: Aug. 3, 2006

(65) Prior Publication Data
US 2008/0249291 A1 Oct. 9, 2008

(51) Int. Cl.
*A01N 43/04* (2006.01)
*A61K 31/70* (2006.01)
*A61K 45/00* (2006.01)
*A61K 47/00* (2006.01)
*C07H 21/02* (2006.01)
*C07H 21/04* (2006.01)

(52) U.S. Cl. ................. 514/44; 536/23.1; 424/278.1
(58) Field of Classification Search ................. None
See application file for complete search history.

(56) References Cited

U.S. PATENT DOCUMENTS

| 6,207,646 B1 * | 3/2001 | Krieg et al. ............ 514/44 |
| 6,406,705 B1 | 6/2002 | Davis et al. |
| 2004/0029129 A1 * | 2/2004 | Wang et al. ............ 435/6 |

FOREIGN PATENT DOCUMENTS

WO 9840100 9/1998

OTHER PUBLICATIONS

Ballas et al. The Journal of Immunology, 2001, 167:4878-4886.*
Akdis, et al., "Immune regulation in atopic dermatitis." Curr Opin Immunol. Dec. 2000;12(6):641-6.
Kwon, et al., "NF-kappaB-dependent regulation of tumor necrosis factor-alpha gene expression by CpG-oligodeoxynucleotides." Biochem Biophys Res Commun. Nov. 7, 2003;311(1):129-38.
Deng, et al., "The features of arthritis induced by CpG motifs in bacterial DNA." Arthritis Rheum. Feb. 2000;43 (2):356-64.
Tanaka, et al., "An antisense oligonucleotide complementary to a sequence in I gamma 2b increases gamma 2b germline transcripts, stimulates B cell DNA synthesis, and inhibits immunoglobulin secretion" J Exp Med. Feb. 1, 1992;175(2):597-607.
Davis, et al., "CpG DNA is a potent enhancer of specific immunity in mice immunized with recombinant hepatitis B surface antigen." J Immunol. Jan. 15, 1998;160(2):870-6.
Rudikoff, et al., "Atopic dermatitis." Lancet. Jun. 6, 1998;351(9117):1715-21.
Imokawa, et al., "Decreased level of ceramides in stratum corneum of atopic dermatitis: an etiologic factor in atopic dry skin?" J Invest Dermatol. Apr. 1991;96(4):523-6.
Ashwell, et al., "Effect of gamma radiation on resting B lymphocytes. I. Oxygen-dependent damage to the plasma membrane results in increased permeability and cell enlargement." J Immunol. May 15, 1986;136(10):3649-56.
Prosser "Survival of human T and B lymphocytes after X-irradiation." Int J Radiat Biol Relat Stud Phys Chem Med. Nov. 1976;30(5):459-65.
Kubota, et al., "Radiation-induced apoptosis in peritoneal resident macrophages of C3H mice" J Radiat Res (Tokyo). Jun. 2004;45(2):205-11.
Krieg, A M, "CpG motifd in bacterial DNA and their immune effects" Annu. Rev. Immunol, 2002, vol. 20:709-742.
Krieg, et al, "CpG motifs in bacterial DNA trigger direct B-cell activation" 1995, nature vol. 374, p. 546-549.
Uhlmann, et al., "Recent advances in the development of immunostimulatory oligonucleotides" Mar. 2003, Current Opinion in Drug Discovery & Development Mar. 2003, vol. 6, No. 2, pp. 204-217.
Krieg, et al., "Mechanism of Action of CpG DNA" Jan. 1, 2000, Current Topics in Microbiology and Immunology, Springer, Berlin, DE, vol. 247, 1, pp. 1-21.
Ballas, et al. "Induction of NK activity in murine and human cells by CpG motifs in oligodeoxynucleotides and bacterial DNA" J Immunol. Sep. 1, 1996;157(5):1840-5.
Klinman, et al. "CpG motifs present in bacteria DNA rapidly induce lymphocytes to secrete interleukin 6, interleukin 12, and interferon gamma" Proc Natl Acad Sci U S A. Apr. 2, 1996;93(7):2879-83.

* cited by examiner

*Primary Examiner* — N. M. Minnifield
*Assistant Examiner* — Oluwatosin Ogunbiyi
(74) *Attorney, Agent, or Firm* — Casimir Jones S.C.

(57) ABSTRACT

Disclosed are oligonucleotides for manipulating an immune reaction. The oligonucleotides of the present invention may be useful to stimulate the immune function, to treat the immune-related diseases and the atopic dermatitis, or to protect the normal immune cells.

8 Claims, 15 Drawing Sheets

FIG. 1

| Sequence | MB DNA (%) | EC DNA (%) | fold (MB/EC) | | | | |
|---|---|---|---|---|---|---|---|
| | | | | GCCGCC= | 0.2336 | 0.0654 | 3.58 |
| | | | | GCCGTC= | 0.1008 | 0.0296 | 3.41 |
| GGCGCC= | 0.1462 | 0.0020 | 73.12 | GGCGGC= | 0.2237 | 0.0662 | 3.38 |
| GCCGGC= | 0.2317 | 0.0062 | 37.19 | GCCGGT= | 0.1302 | 0.0402 | 3.24 |
| GTCGAC= | 0.0990 | 0.0116 | 8.56 | CCCGGC= | 0.1183 | 0.0365 | 3.24 |
| CTCGAG= | 0.0299 | 0.0038 | 7.96 | GACGGC= | 0.1033 | 0.0327 | 3.16 |
| CCCGGG= | 0.0645 | 0.0091 | 7.13 | CCCGCG= | 0.0824 | 0.0263 | 3.13 |
| CACGTG= | 0.0205 | 0.0030 | 6.74 | GCCGGG= | 0.1165 | 0.0373 | 3.13 |
| CCCGAG= | 0.0451 | 0.0069 | 6.58 | CGCGGG= | 0.0849 | 0.0273 | 3.11 |
| CTCGGG= | 0.0392 | 0.0068 | 5.75 | ACCGGC= | 0.1242 | 0.0405 | 3.07 |
| GCCGAC= | 0.1435 | 0.0297 | 4.83 | GGCGGG= | 0.0982 | 0.0323 | 3.04 |
| GTCGGC= | 0.1400 | 0.0295 | 4.74 | CCCGCC= | 0.0995 | 0.0329 | 3.02 |
| CTCGGC= | 0.1021 | 0.0217 | 4.71 | CGCGGT= | 0.1117 | 0.0372 | 3.00 |
| GCCGAG= | 0.1000 | 0.0218 | 4.58 | ACCGCG= | 0.1090 | 0.0368 | 2.97 |
| GACGAG= | 0.0493 | 0.0120 | 4.10 | ACCGAG= | 0.0511 | 0.0175 | 2.92 |
| GCCGCG= | 0.1781 | 0.0435 | 4.09 | GTCGGA= | 0.0331 | 0.0118 | 2.80 |
| GACGTC= | 0.0619 | 0.0151 | 4.09 | GGCGAC= | 0.1005 | 0.0360 | 2.80 |
| GTCGAG= | 0.0677 | 0.0166 | 4.08 | CTCGGT= | 0.0494 | 0.0178 | 2.78 |
| GTCGTC= | 0.0755 | 0.0192 | 3.93 | GTCGCC= | 0.1056 | 0.0383 | 2.76 |
| CTCGAC= | 0.0643 | 0.0165 | 3.90 | GTCGCG= | 0.0884 | 0.0323 | 2.74 |
| CCCGAC= | 0.0676 | 0.0175 | 3.86 | CACGTC= | 0.0430 | 0.0158 | 2.73 |
| CTCGTC= | 0.0501 | 0.0130 | 3.86 | TCCGAC= | 0.0326 | 0.0121 | 2.70 |
| CGCGGC= | 0.1751 | 0.0455 | 3.85 | CGCGAC= | 0.0852 | 0.0320 | 2.66 |
| GTCGGG= | 0.0627 | 0.0165 | 3.79 | | | | |
| TCCGAG= | 0.0203 | 0.0054 | 3.78 | | | | |
| GACGAC= | 0.0747 | 0.0199 | 3.76 | Average | 0.0498 | 0.0288 | |
| CTCGGA= | 0.0202 | 0.0054 | 3.73 | Sum | 12.7440 | 7.3665 | |

FIG. 2 a) MB-ODN 4/5 (-CGXXCGXXXCG-) — SEQUENCE ID No.: 16

| No. | Sequence | Score | SEQ ID |
|---|---|---|---|
| 1 | CTCCAcgGGcgGCAcgGCCA | 11811 | 17 |
| 2 | TGTCTcgGGcgGCAcgGTTG | 11773 | 18 |
| 3 | CAAGGcgGTcgGCTcgATGG | 11538 | 19 |
| 4 | AACTGcgGAcgTGGcgGCAG | 10931 | 20 |
| 5 | GTCAGcgGAcgTGGcgGCTC | 10829 | 21 |
| 6 | AAAGGcgTGcgGGTcgGCCC | 10697 | 22 |
| 7 | CTCAGcgGGcgGCAcgTGCA | 10670 | 23 |
| 8 | CACAAcgGGcgCCTcgGGTT | 10319 | 24 |
| 9 | ATGAAcgGGcgGCTcgAGCC | 10240 | 25 |
| 10 | GATGGcgATcgGCAcgCCCA | 10199 | 26 |
| 11 | CAGCAcgTGcgTGGcgGGAT | 9962 | 27 |
| 12 | GCTGGcgGGcgAGGcgATTC | 9855 | 28 |
| 13 | TGTTGcgCTcgGCTcgGCAG | 9839 | 29 |
| 14 | GGTGGcgGTcgAGGcgCTCT | 9728 | 30 |
| 15 | GGTGGcgCAcgCCTcgGCCC | 9259 | 31 |
| 16 | GGGGGcgGTcgCCTcgCTAA | 9250 | 32 |
| 17 | GACATcgGTcgGCAcgTCAG | 9098 | 33 |
| 18 | CCAGTcgGGcgGGGcgCTGG | 9022 | 34 |
| 19 | TCTGGcgGTcgAAGcgGCCC | 8953 | 35 |
| 20 | CAACTcgATcgGGGcgCCCA | 8878 | 36 |
| 21 | TTTGGcgGTcgGTGcgCAGC | 8869 | 37 |
| 22 | CCAGcgGTcgGTGcgCAGG | 8869 | 38 |
| 23 | CTCCTcgGTcgAGGcgGTGG | 8844 | 39 |
| 24 | ACCATcgGGcgCCAcgTCTC | 8780 | 40 |
| 25 | CAACAcgATcgTGTcgGCTG | 8615 | 41 |
| 393 | GTGTTcgAAcgCTAcgAACC | 1681 | 42 |
| 394 | AAGTAcgAAcgATGcgAGAA | 1637 | 43 |
| 395 | ACTAGcgTAcgCAGcgAATC | 1539 | 44 | b) MB-ODN 5/5 (-CGXXXCGXXXCG-) — SEQUENCE ID No.: 45

| No. | Sequence | Score | SEQ ID |
|---|---|---|---|
| 1 | TGCTcgTGGcgGCTcgGCAG | 12868 | 46 |
| 2 | GAGGcgGCTcgGTGcgGGTC | 12599 | 47 |
| 3 | TTGGcgGCAcgCAAcgCCTC | 11345 | 48 |
| 4 | GAAGcgTTGcgGGGcgGCCC | 11280 | 49 |
| 5 | AAGGcgTGGcgGCTcgTGGA | 11258 | 50 |
| 6 | CAGGcgATGcgCCTcgGCTC | 10614 | 51 |
| 7 | GTTGcgGGAcgAGTcgGCAT | 10297 | 52 |
| 8 | GGGGcgGGTcgACTcgACCA | 10243 | 53 |
| 9 | TGGTcgGGGcgGGTcgACTC | 10153 | 54 |
| 10 | ATCAcgCTAcgGGGcgGCCA | 10063 | 55 |
| 11 | GTGGcgCCAcgAGTcgACAT | 10059 | 56 |
| 12 | AAGGcgGTCcgCATcgATGG | 10036 | 57 |
| 13 | GAGGcgGGGcgGGTcgATCT | 9743 | 58 |
| 14 | AATTcgTGGcgGCTcgTGCA | 9712 | 59 |
| 15 | CAGGcgTGcgGTGcgGCAT | 9657 | 60 |
| 16 | TAGGcgCTTcgAGTcgGCAC | 9655 | 61 |
| 17 | GTGAcgTCAcgGGTcgGCAG | 9390 | 62 |
| 18 | GCTTcgAGTcgGCAcgCCAG | 9269 | 63 |
| 19 | GTGTcgGGGcgAGGcgACCA | 9164 | 64 |
| 20 | TTGGcgTTGcgTGTcgGCCT | 9034 | 65 |
| 21 | TCATcgATGcgGGGcgCCAC | 8959 | 66 |
| 22 | GAGGcgGGcgGGGcgGAGA | 8873 | 67 |
| 23 | TAGGcgATGcgCAGcgCCTG | 8845 | 68 |
| 24 | CAGGcgGTGcgGCAcgCAGT | 8703 | 69 |
| 25 | CTGAcgCCTcgGCTcgAGCT | 8642 | 70 |
| 552 | ATTAcgCTGcgAAAcgCAGT | 1807 | 71 |
| 553 | TAATcgGAAcgTAAcgATCC | 1743 | 72 |
| 554 | CATGcgTAAcgTTAcgGAAA | 1219 | 73 |

FIG. 3 a) MB-ODN 4/5 (-CGXXCGXXXCG-) SEQUENCE ID No.: 74

| ODN | Sequence | |
|---|---|---|
| MB-ODN4/5-1 | CCAGTCGGCGGGGCGCTGG | 75 |
| MB-ODN4/5-2 | GCTGCGGCGCAGGCCATTC | 76 |
| MB-ODN4/5-3 | ACCAGCGGCGACTCGCCTG | 77 |
| MB-ODN4/5-4 | GGTGGCGGGCGTTGCGCATC | 78 |
| MB-ODN4/5-5 | GGCAGCGGCGCATCGCCAG | 79 |
| MB-ODN4/5-6 | CTTGGCGGCGCTGCCACCA | 80 |
| MB-ODN4/5-7 | AACTGCGGACGTGGCGGCAG | 81 |
| MB-ODN4/5-8 | GGTCACGCTCGGATCGATTC | 82 |
| MB-ODN4/5-9 | TTTGGCGGTCGGTGCGCAGC | 83 |
| MB-ODN4/5-10 | GGTGGCGGTCGAGGCGCTCT | 84 |
| MB-ODN4/5-11 | CGTGGCCGTCGAGGCGCTCT | 85 |
| MB-ODN4/5-12 | TTTGTCGGTCGCAACGAAAA | 86 |
| MB-ODN4/5-13 | GATGTCGAGCGGATCGGCAC | 87 |
| MB-ODN4/5-14 | TTGCTCGAGCGGTTCGGCAT | 88 |
| MB-ODN4/5-15 | TTCGTCGAGCCTGTCGGCTG | 89 |
| MB-ODN4/5-16 | AGCATCGAGCGCAGCGTGGT | 90 |
| MB-ODN4/5-17 | GGCAGCCAGCGCAACGACAC | 91 |
| MB-ODN4/5-18 | CTCATCGAGCGCCACGGCAG | 92 |
| MB-ODN4/5-19 | ATGCTCGAGCGCCTCGGCCT | 93 |
| MB-ODN4/5-20 | GCCTTCGAACGGGTCGAGGG | 94 |
| MB-ODN4/5-21 | GATGGCGAACGTCACGTCAT | 95 |
| MB-ODN4/5-22 | CTTGTCGAACGTCTCGGCCA | 96 |
| MB-ODN4/5-23 | GAGATCGAACGCTTCGACAC | 97 |
| MB-ODN4/5-24 | CAGTTCGATCGAGACGACCC | 98 |
| MB-ODN4/5-25 | GTAGCCATCGATCGCGCCAA | 99 |
| MB-ODN4/5-26 | CAACACGATCGTGTCGGCTG | 100 |
| MB-ODN4/5-27 | CTAGGCGATCGCAACGAAGT | 101 |
| MB-ODN4/5-28 | CCACACGATCGCCACGGTGG | 102 |
| MB-ODN4/5-29 | GGCAGCGTGCGTGACGACTT | 103 |
| MB-ODN4/5-30 | TAAGGCGTGCGCATCGATAT | 104 |
| MB-ODN4/5-31 | AGCAGCGTTCGTGTCGGCCT | 105 |
| MB-ODN4/5-32 | TGTTGCGCACGGTGCGCTGC | 106 |
| MB-ODN4/5-33 | CTGGCGCACGCACGCACGCTGG | 107 |
| MB-ODN4/5-34 | GGCAGCGCACGCAGCGCAAC | 108 |
| MB-ODN4/5-35 | GCAGGCGCTCGTCACGCCCC | 109 | b) MB-ODN 5/5 (-CGXXXCGXXXCG-) SEQUENCE ID No.: 110

| ODN | Sequence | |
|---|---|---|
| MB-ODN5/5-1 | GATGCCGATCGGTGCCGCTGC | 111 |
| MB-ODN5/5-2 | CAGGCGGTGCGCAACGCCCTG | 112 |
| MB-ODN5/5-3 | GATGCGGTGCGCATCGCCCAA | 113 |
| MB-ODN5/5-4 | GACGCCGTGCGCCACGCTGCT | 114 |
| MB-ODN5/5-5 | GGACCGCTCGACACCGACAA | 115 |
| MB-ODN5/5-6 | TGGTCGAGCGCTTGCGGCAC | 116 |
| MB-ODN5/5-7 | ACAGCGAGTCGCTGCGCCAC | 117 |
| MB-ODN5/5-8 | TAGGCGAAGCGATGCGGCCC | 118 |
| MB-ODN5/5-9 | TCAGCGAAGCGGTGCGCCCA | 119 |
| MB-ODN5/5-10 | ATCTCGAAGCGCTGCAGGG | 120 |
| MB-ODN5/5-11 | GGGTCGAATCGTGTCGCCTC | 121 |
| MB-ODN5/5-12 | TAGGCGATGCGCAGCGCCTG | 122 |
| MB-ODN5/5-13 | ATGGCGATGCGCTGCGCCTG | 123 |
| MB-ODN5/5-14 | GGGTCGACACGCTGCGATTG | 124 |
| MB-ODN5/5-15 | TGCTCGTGGCGGCTCGGCAG | 125 |
| MB-ODN5/5-16 | CCAGCGTGGCGATGCCGGCA | 126 |
| MB-ODN5/5-17 | GCATCGTGGCGCAGCGCATG | 127 |
| MB-ODN5/5-18 | TGGACGTGTCGTAGCGCAGG | 128 |
| MB-ODN5/5-19 | CTGGCGTAGCGCCTCGGCCT | 129 |
| MB-ODN5/5-20 | TTGGCGTTGCGTGTCGGCCT | 130 |
| MB-ODN5/5-21 | AAATCGTTGCGGCACGGCAT | 131 |
| MB-ODN5/5-22 | ATCACGTTGCGCAGCGGGTG | 132 |
| MB-ODN5/5-23 | AAATCGTCTCGAGGCGTTCC | 133 |
| MB-ODN5/5-24 | GTGGCGCAGCGTGGCGGTGG | 134 |
| MB-ODN5/5-25 | TGGGCGCAGCGGCACGCTAT | 135 |
| MB-ODN5/5-26 | TCTGCGCAGCGCATCGTTGA | 136 |
| MB-ODN5/5-27 | TGGGCGCAGCGTTACCAACT | 137 |
| MB-ODN5/5-28 | GCCTCGCAGCGACACCGTTCC | 138 |
| MB-ODN5/5-29 | TTGGCGCAACGCATCGGAGA | 139 |
| MB-ODN5/5-30 | GGAGCGCAACGTTGCGCATC | 140 |
| MB-ODN5/5-31 | ACAACGCATCGCATCGAGGA | 141 |
| MB-ODN5/5-32 | AGCACGCTGCGGCGTCAG | 142 |
| MB-ODN5/5-33 | ACTGCGCTGCGGCACGACCC | 143 |
| MB-ODN5/5-34 | GTCTCGCTGCGCAGCGGGT | 144 |
| MB-ODN5/5-35 | GGGACGCTGCGTGACGTGT | 145 |
| MB-ODN5/5-36 | CTCACGCCTCGGCTCGAGCT | 146 |

FIG. 6

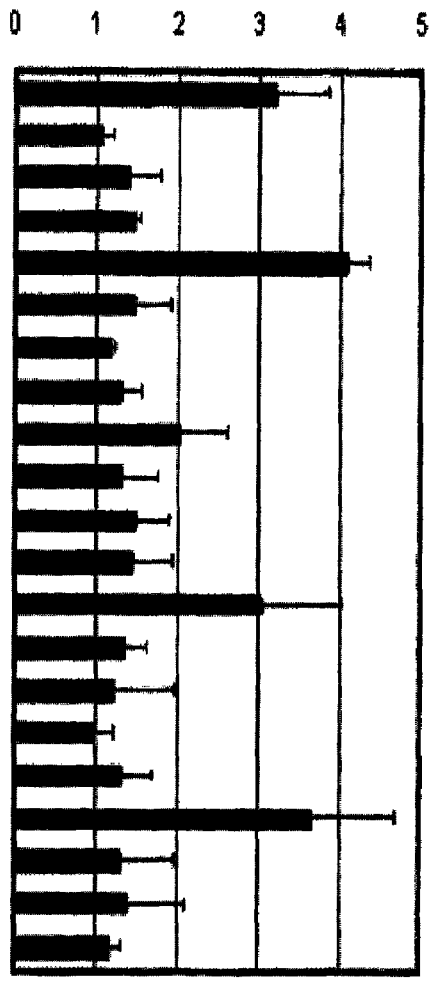

a)

| ODN | Sequence | SEQUENCE ID No.: |
|---|---|---|
| MB-ODN 31(O) | AGCAGCGTTCGTGTCGGCCT | 165 |
| MB-ODN 31(M) | AGCGTTCGTGTCGGC | 166 |
| #31-CG-1 | AGCAGGCTTCGTGTCGGCCT | 167 |
| #31-CG-2 | AGCAGCGTTGCTGTCGGCCT | 168 |
| #31-CG-3 | AGCAGCGTTCGTGTGCGCCT | 169 |
| #31-CG-4 | AGCAGGCTTGCTGTCGGCCT | 170 |
| #31-CG-5 | AGCAGGCTTCGTGTGCGCCT | 171 |
| #31-CG-6 | AGCAGCGTTGCTGTGCGCCT | 172 |
| #31-CG-7 | AGCAGGCTTGCTGTGCGCCT | 173 |
| #31-A-1 | AGCAGCATTCGTGTCGGCCT | 174 |
| #31-A-2 | AGCAGCTTTCGTGTCGGCCT | 175 |
| #31-A-3 | AGCAGCCTTCGTGTCGGCCT | 176 |
| #31-B-1 | AGCAGCGTTCATGTCGGCCT | 177 |
| #31-B-2 | AGCAGCGTTCTTGTCGGCCT | 178 |
| #31-B-3 | AGCAGCGTTCCTGTCGGCCT | 179 |
| #31-C-1 | AGCAGCGTTCGTGTCAGCCT | 180 |
| #31-C-2 | AGCAGCGTTCGTGTCTGCCT | 181 |
| #31-C-3 | AGCAGCGTTCGTGTCCGCCT | 182 |
| #31-D-1 | AGCAGCATTCATGTCGGCCT | 183 |
| #31-D-2 | AGCAGCATTCGTGTCAGCCT | 184 |
| #31-D-3 | AGCAGCGTTCATGTCAGCCT | 185 | b) Fold Activation (phIL-8-Luc)

FIG. 8
a)
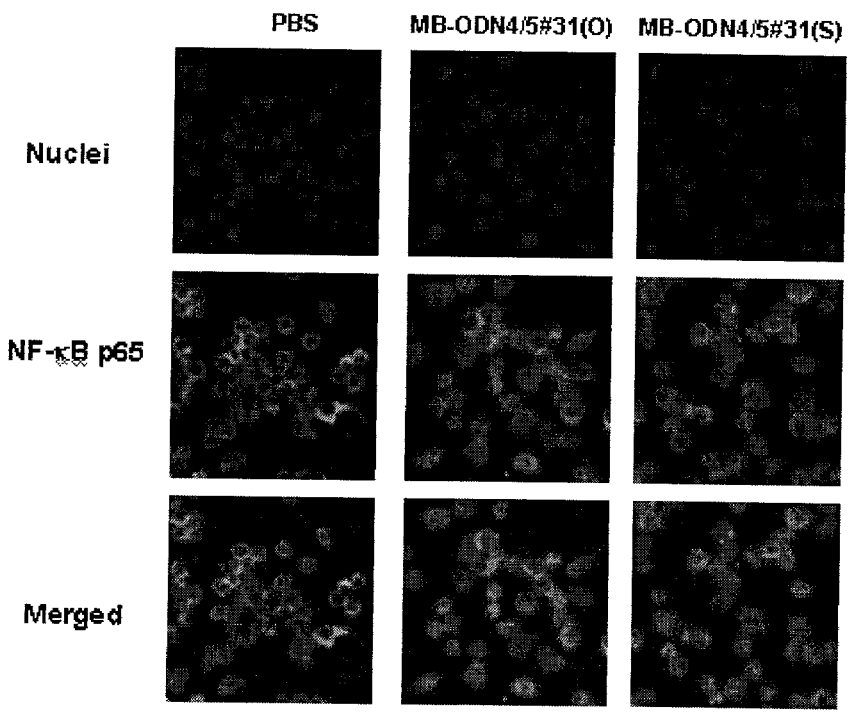
b)
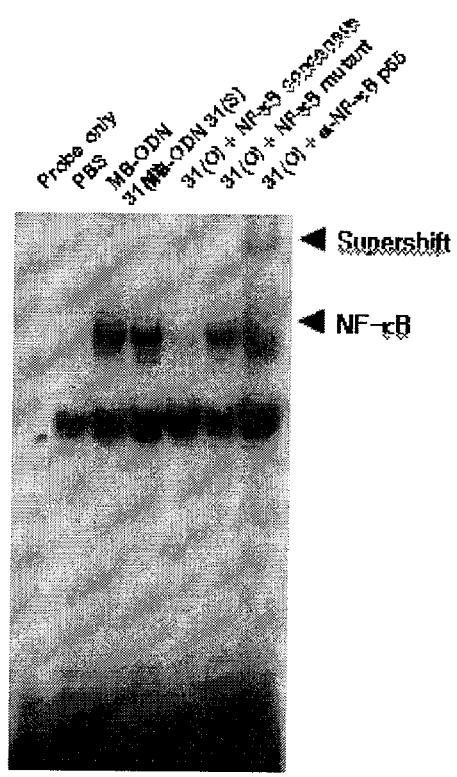

SEQUENCE LISTING

<160> NUMBER OF SEQ ID NOS: 187

<210> SEQ ID NO 1
<211> LENGTH: 15
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, c, or t
<220> FEATURE:
<221> NAME/KEY: misc_feature
<222> LOCATION: (2)..(2)
<223> OTHER INFORMATION: n is g or t
<220> FEATURE:
<221> NAME/KEY: misc_feature
<222> LOCATION: (8)..(8)
<223> OTHER INFORMATION: n is a or g
<220> FEATURE:
<221> NAME/KEY: misc_feature
<222> LOCATION: (13)..(13)
<223> OTHER INFORMATION: n is c or g
<220> FEATURE:
<221> NAME/KEY: misc_feature
<222> LOCATION: (15)..(15)
<223> OTHER INFORMATION: n is a or c

<400> SEQUENCE: 1
nncgttcntg tcngn                                                     15

<210> SEQ ID NO 2
<211> LENGTH: 20
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(1)
<223> OTHER INFORMATION: n is a, g, or t
<220> FEATURE:
<221> NAME/KEY: misc_feature
<222> LOCATION: (2)..(2)
<223> OTHER INFORMATION: n is g or t
<220> FEATURE:
<221> NAME/KEY: misc_feature
<222> LOCATION: (3)..(3)
<223> OTHER INFORMATION: n is a or c
<220> FEATURE:
<221> NAME/KEY: misc_feature
<222> LOCATION: (4)..(4)
<223> OTHER INFORMATION: n is a, c, or t
<220> FEATURE:
<221> NAME/KEY: misc_feature
<222> LOCATION: (5)..(5)
<223> OTHER INFORMATION: n is g or t
<220> FEATURE:
<221> NAME/KEY: misc_feature
<222> LOCATION: (11)..(11)
<223> OTHER INFORMATION: n is a or g
<220> FEATURE:
<221> NAME/KEY: misc_feature
<222> LOCATION: (16)..(16)
<223> OTHER INFORMATION: n is c or g
<220> FEATURE:
<221> NAME/KEY: misc_feature
<222> LOCATION: (18)..(18)
<223> OTHER INFORMATION: n is a or c
<220> FEATURE:
<221> NAME/KEY: misc_feature
<222> LOCATION: (19)..(19)
<223> OTHER INFORMATION: n is c or t
<220> FEATURE:

```
<221> NAME/KEY: misc_feature
<222> LOCATION: (20)..(20)
<223> OTHER INFORMATION: n is g or t

<400> SEQUENCE: 2
nnnnncgttc ntgtcngnnn                                              20

<210> SEQ ID NO 3
<211> LENGTH: 20
<212> TYPE: DNA
<213> ORGANISM: Artificial Sequence
<220> FEATURE:
<223> OTHER INFORMATION: Synthetic

<400> SEQUENCE: 3
agcagcgttc gtgtcggcct                                              20

<210> SEQ ID NO 4
<211> LENGTH: 20
<212> TYPE: DNA
<213> ORGANISM: Artificial Sequence
<220> FEATURE:
<223> OTHER INFORMATION: Synthetic

<400> SEQUENCE: 4
agcagcgttc gtgtgcgcct                                              20

<210> SEQ ID NO 5
<211> LENGTH: 20
<212> TYPE: DNA
<213> ORGANISM: Artificial Sequence
<220> FEATURE:
<223> OTHER INFORMATION: Synthetic

<400> SEQUENCE: 5
agcagcgttc atgtcggcct                                              20

<210> SEQ ID NO 6
<211> LENGTH: 20
<212> TYPE: DNA
<213> ORGANISM: Artificial Sequence
<220> FEATURE:
<223> OTHER INFORMATION: Synthetic

<400> SEQUENCE: 6
agcagcgttc gtgtccgcct                                              20

<210> SEQ ID NO 7
<211> LENGTH: 20
<212> TYPE: DNA
<213> ORGANISM: Artificial Sequence
<220> FEATURE:
<223> OTHER INFORMATION: Synthetic

<400> SEQUENCE: 7
gtattcgttc gtgtcgtcct                                              20

<210> SEQ ID NO 8
<211> LENGTH: 20
<212> TYPE: DNA
<213> ORGANISM: Artificial Sequence
<220> FEATURE:
<223> OTHER INFORMATION: Synthetic

<400> SEQUENCE: 8
tgactcgttc gtgtcgcatg                                              20
```

<210> SEQ ID NO 9
<211> LENGTH: 27
<212> TYPE: DNA
<213> ORGANISM: Artificial Sequence
<220> FEATURE:
<223> OTHER INFORMATION: Synthetic

<400> SEQUENCE: 9
gtgagatctg aagtgtgatg actcagg                                              27

<210> SEQ ID NO 10
<211> LENGTH: 27
<212> TYPE: DNA
<213> ORGANISM: Artificial Sequence
<220> FEATURE:
<223> OTHER INFORMATION: Synthetic

<400> SEQUENCE: 10
gtgaagcttg aagcttgtgt gctctgc                                              27

<210> SEQ ID NO 11
<211> LENGTH: 25
<212> TYPE: DNA
<213> ORGANISM: Artificial Sequence
<220> FEATURE:
<223> OTHER INFORMATION: Synthetic

<400> SEQUENCE: 11
catgagctca gcctcccgtc tgacc                                                25

<210> SEQ ID NO 12
<211> LENGTH: 25
<212> TYPE: DNA
<213> ORGANISM: Artificial Sequence
<220> FEATURE:
<223> OTHER INFORMATION: Synthetic

<400> SEQUENCE: 12
ctgggctcga gggagagtcc aatgg                                                25

<210> SEQ ID NO 13
<211> LENGTH: 22
<212> TYPE: DNA
<213> ORGANISM: Artificial Sequence
<220> FEATURE:
<223> OTHER INFORMATION: Synthetic

<400> SEQUENCE: 13
agttgagggg actttcccag gc                                                   22

<210> SEQ ID NO 14
<211> LENGTH: 19
<212> TYPE: DNA
<213> ORGANISM: Artificial Sequence
<220> FEATURE:
<223> OTHER INFORMATION: Synthetic

<400> SEQUENCE: 14
ctggtgcaaa gaaacatgg                                                       19

<210> SEQ ID NO 15
<211> LENGTH: 20
<212> TYPE: DNA
<213> ORGANISM: Artificial Sequence
<220> FEATURE:
<223> OTHER INFORMATION: Synthetic

```
<400> SEQUENCE: 15
tggtttgatg atgtccctga                                          20

<210> SEQ ID NO 16
<211> LENGTH: 11
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t

<400> SEQUENCE: 16
cgnncgnnnc g                                                   11

<210> SEQ ID NO 17
<211> LENGTH: 20
<212> TYPE: DNA
<213> ORGANISM: Artificial Sequence
<220> FEATURE:
<223> OTHER INFORMATION: Synthetic

<400> SEQUENCE: 17
ctccacgggc ggcacggcca                                          20

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
tgtctcgggc ggcacggttg                                          20

<210> SEQ ID NO 19
<211> LENGTH: 20
<212> TYPE: DNA
<213> ORGANISM: Artificial Sequence
<220> FEATURE:
<223> OTHER INFORMATION: Synthetic

<400> SEQUENCE: 19
caaggcggtc ggctcgatgg                                          20

<210> SEQ ID NO 20
<211> LENGTH: 20
<212> TYPE: DNA
<213> ORGANISM: Artificial Sequence
<220> FEATURE:
<223> OTHER INFORMATION: Synthetic

<400> SEQUENCE: 20
aactgcggac gtggcggcag                                          20

<210> SEQ ID NO 21
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 21
gtcagcggac gtggcggctc                                              20

<210> SEQ ID NO 22
<211> LENGTH: 20
<212> TYPE: DNA
<213> ORGANISM: Artificial Sequence
<220> FEATURE:
<223> OTHER INFORMATION: Synthetic

<400> SEQUENCE: 22
aaaggcgtgc gggtcggccc                                              20

<210> SEQ ID NO 23
<211> LENGTH: 20
<212> TYPE: DNA
<213> ORGANISM: Artificial Sequence
<220> FEATURE:
<223> OTHER INFORMATION: Synthetic

<400> SEQUENCE: 23
ctcagcgggc ggcacgtgca                                              20

<210> SEQ ID NO 24
<211> LENGTH: 20
<212> TYPE: DNA
<213> ORGANISM: Artificial Sequence
<220> FEATURE:
<223> OTHER INFORMATION: Synthetic

<400> SEQUENCE: 24
cacaacgggc gcctcggctt                                              20

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
atgaacgggc ggctcgagcc                                              20

<210> SEQ ID NO 26
<211> LENGTH: 20
<212> TYPE: DNA
<213> ORGANISM: Artificial Sequence
<220> FEATURE:
<223> OTHER INFORMATION: Synthetic

<400> SEQUENCE: 26
gatggcgatc ggcacgccca                                              20

<210> SEQ ID NO 27
<211> LENGTH: 20
<212> TYPE: DNA
<213> ORGANISM: Artificial Sequence
<220> FEATURE:
<223> OTHER INFORMATION: Synthetic

<400> SEQUENCE: 27
cagcacgtgc gtggcggcat                                              20

<210> SEQ ID NO 28
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 28
gctggcgggc gaggcgattc                                              20

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
tgttgcgctc ggctcggcag                                              20

<210> SEQ ID NO 30
<211> LENGTH: 20
<212> TYPE: DNA
<213> ORGANISM: Artificial Sequence
<220> FEATURE:
<223> OTHER INFORMATION: Synthetic

<400> SEQUENCE: 30
ggtggcggtc gaggcgctct                                              20

<210> SEQ ID NO 31
<211> LENGTH: 20
<212> TYPE: DNA
<213> ORGANISM: Artificial Sequence
<220> FEATURE:
<223> OTHER INFORMATION: Synthetic

<400> SEQUENCE: 31
ggtggcgcac gcctcggccc                                              20

<210> SEQ ID NO 32
<211> LENGTH: 20
<212> TYPE: DNA
<213> ORGANISM: Artificial Sequence
<220> FEATURE:
<223> OTHER INFORMATION: Synthetic

<400> SEQUENCE: 32
gggggcggtc gcctcgctaa                                              20

<210> SEQ ID NO 33
<211> LENGTH: 20
<212> TYPE: DNA
<213> ORGANISM: Artificial Sequence
<220> FEATURE:
<223> OTHER INFORMATION: Synthetic

<400> SEQUENCE: 33
gacatcggtc ggcacgtcag                                              20

<210> SEQ ID NO 34
<211> LENGTH: 20
<212> TYPE: DNA
<213> ORGANISM: Artificial Sequence
<220> FEATURE:
<223> OTHER INFORMATION: Synthetic

<400> SEQUENCE: 34
ccagtcgggc ggggcgctgg                                              20
```

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
tctggcggtc gaagcggccc                                           20

<210> SEQ ID NO 36
<211> LENGTH: 20
<212> TYPE: DNA
<213> ORGANISM: Artificial Sequence
<220> FEATURE:
<223> OTHER INFORMATION: Synthetic

<400> SEQUENCE: 36
caactcgatc ggggcgccca                                           20

<210> SEQ ID NO 37
<211> LENGTH: 20
<212> TYPE: DNA
<213> ORGANISM: Artificial Sequence
<220> FEATURE:
<223> OTHER INFORMATION: Synthetic

<400> SEQUENCE: 37
tttggcggtc ggtgcgcagc                                           20

<210> SEQ ID NO 38
<211> LENGTH: 20
<212> TYPE: DNA
<213> ORGANISM: Artificial Sequence
<220> FEATURE:
<223> OTHER INFORMATION: Synthetic

<400> SEQUENCE: 38
ccaggcggtc ggtgcgcagg                                           20

<210> SEQ ID NO 39
<211> LENGTH: 20
<212> TYPE: DNA
<213> ORGANISM: Artificial Sequence
<220> FEATURE:
<223> OTHER INFORMATION: Synthetic

<400> SEQUENCE: 39
ctcctcggtc gaggcggtgg                                           20

<210> SEQ ID NO 40
<211> LENGTH: 20
<212> TYPE: DNA
<213> ORGANISM: Artificial Sequence
<220> FEATURE:
<223> OTHER INFORMATION: Synthetic

<400> SEQUENCE: 40
accatcgggc gccacgtctc                                           20

<210> SEQ ID NO 41
<211> LENGTH: 20
<212> TYPE: DNA
<213> ORGANISM: Artificial Sequence
<220> FEATURE:
<223> OTHER INFORMATION: Synthetic

```
<400> SEQUENCE: 41
caacacgatc gtgtcggctg                                                  20

<210> SEQ ID NO 42
<211> LENGTH: 20
<212> TYPE: DNA
<213> ORGANISM: Artificial Sequence
<220> FEATURE:
<223> OTHER INFORMATION: Synthetic

<400> SEQUENCE: 42
gtgttcgaac gctacgaacc                                                  20

<210> SEQ ID NO 43
<211> LENGTH: 20
<212> TYPE: DNA
<213> ORGANISM: Artificial Sequence
<220> FEATURE:
<223> OTHER INFORMATION: Synthetic

<400> SEQUENCE: 43
aagtacgaac gatgcgagaa                                                  20

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
actagcgtac gcagcgaatc                                                  20

<210> SEQ ID NO 45
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 45
cgnnncgnnn cg                                                          12

<210> SEQ ID NO 46
<211> LENGTH: 20
<212> TYPE: DNA
<213> ORGANISM: Artificial Sequence
<220> FEATURE:
<223> OTHER INFORMATION: Synthetic

<400> SEQUENCE: 46
tgctcgtggc ggctcggcag                                                  20

<210> SEQ ID NO 47
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 47
gaggcggctc ggtgcgggtc                                               20

<210> SEQ ID NO 48
<211> LENGTH: 20
<212> TYPE: DNA
<213> ORGANISM: Artificial Sequence
<220> FEATURE:
<223> OTHER INFORMATION: Synthetic

<400> SEQUENCE: 48
ttggcggcac gcaacgcctc                                               20

<210> SEQ ID NO 49
<211> LENGTH: 20
<212> TYPE: DNA
<213> ORGANISM: Artificial Sequence
<220> FEATURE:
<223> OTHER INFORMATION: Synthetic

<400> SEQUENCE: 49
gaagcgttgc ggggcggccc                                               20

<210> SEQ ID NO 50
<211> LENGTH: 20
<212> TYPE: DNA
<213> ORGANISM: Artificial Sequence
<220> FEATURE:
<223> OTHER INFORMATION: Synthetic

<400> SEQUENCE: 50
aaggcgtggc ggctcgtgga                                               20

<210> SEQ ID NO 51
<211> LENGTH: 20
<212> TYPE: DNA
<213> ORGANISM: Artificial Sequence
<220> FEATURE:
<223> OTHER INFORMATION: Synthetic

<400> SEQUENCE: 51
caggcgatgc gcctcggctc                                               20

<210> SEQ ID NO 52
<211> LENGTH: 20
<212> TYPE: DNA
<213> ORGANISM: Artificial Sequence
<220> FEATURE:
<223> OTHER INFORMATION: Synthetic

<400> SEQUENCE: 52
gttgcgggac gagtcggcat                                               20

<210> SEQ ID NO 53
<211> LENGTH: 20
<212> TYPE: DNA
<213> ORGANISM: Artificial Sequence
<220> FEATURE:
<223> OTHER INFORMATION: Synthetic

<400> SEQUENCE: 53
ggggcgggtc gactcgacca                                               20

<210> SEQ ID NO 54
<211> LENGTH: 20
<212> TYPE: DNA
```

<213> ORGANISM: Artificial Sequence
<220> FEATURE:
<223> OTHER INFORMATION: Synthetic

<400> SEQUENCE: 54
tggtcggggc gggtcgactc                                                    20

<210> SEQ ID NO 55
<211> LENGTH: 20
<212> TYPE: DNA
<213> ORGANISM: Artificial Sequence
<220> FEATURE:
<223> OTHER INFORMATION: Synthetic

<400> SEQUENCE: 55
atcacgctac ggggcggcca                                                    20

<210> SEQ ID NO 56
<211> LENGTH: 20
<212> TYPE: DNA
<213> ORGANISM: Artificial Sequence
<220> FEATURE:
<223> OTHER INFORMATION: Synthetic

<400> SEQUENCE: 56
gtggcgccac gagtcgacat                                                    20

<210> SEQ ID NO 57
<211> LENGTH: 20
<212> TYPE: DNA
<213> ORGANISM: Artificial Sequence
<220> FEATURE:
<223> OTHER INFORMATION: Synthetic

<400> SEQUENCE: 57
aaggcggctc gcatcgatgg                                                    20

<210> SEQ ID NO 58
<211> LENGTH: 20
<212> TYPE: DNA
<213> ORGANISM: Artificial Sequence
<220> FEATURE:
<223> OTHER INFORMATION: Synthetic

<400> SEQUENCE: 58
gaggcggggc gggtcgatct                                                    20

<210> SEQ ID NO 59
<211> LENGTH: 20
<212> TYPE: DNA
<213> ORGANISM: Artificial Sequence
<220> FEATURE:
<223> OTHER INFORMATION: Synthetic

<400> SEQUENCE: 59
aattcgtggc ggctcgtgca                                                    20

<210> SEQ ID NO 60
<211> LENGTH: 20
<212> TYPE: DNA
<213> ORGANISM: Artificial Sequence
<220> FEATURE:
<223> OTHER INFORMATION: Synthetic

<400> SEQUENCE: 60
caggcggtgc ggtgcggcat                                                    20

```
<210> SEQ ID NO 61
<211> LENGTH: 20
<212> TYPE: DNA
<213> ORGANISM: Artificial Sequence
<220> FEATURE:
<223> OTHER INFORMATION: Synthetic

<400> SEQUENCE: 61
taggcgcttc gagtcggcag                                                    20

<210> SEQ ID NO 62
<211> LENGTH: 20
<212> TYPE: DNA
<213> ORGANISM: Artificial Sequence
<220> FEATURE:
<223> OTHER INFORMATION: Synthetic

<400> SEQUENCE: 62
gtgacgtcac gggtcggcag                                                    20

<210> SEQ ID NO 63
<211> LENGTH: 20
<212> TYPE: DNA
<213> ORGANISM: Artificial Sequence
<220> FEATURE:
<223> OTHER INFORMATION: Synthetic

<400> SEQUENCE: 63
gcttcgagtc ggcacgccag                                                    20

<210> SEQ ID NO 64
<211> LENGTH: 20
<212> TYPE: DNA
<213> ORGANISM: Artificial Sequence
<220> FEATURE:
<223> OTHER INFORMATION: Synthetic

<400> SEQUENCE: 64
gtgtcggggc gaggcgacca                                                    20

<210> SEQ ID NO 65
<211> LENGTH: 20
<212> TYPE: DNA
<213> ORGANISM: Artificial Sequence
<220> FEATURE:
<223> OTHER INFORMATION: Synthetic

<400> SEQUENCE: 65
ttggcgttgc gtgtcggcct                                                    20

<210> SEQ ID NO 66
<211> LENGTH: 20
<212> TYPE: DNA
<213> ORGANISM: Artificial Sequence
<220> FEATURE:
<223> OTHER INFORMATION: Synthetic

<400> SEQUENCE: 66
tcatcgatgc ggggcgccac                                                    20

<210> SEQ ID NO 67
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 67
gaggcggggc ggggcggaga                                                    20

<210> SEQ ID NO 68
<211> LENGTH: 20
<212> TYPE: DNA
<213> ORGANISM: Artificial Sequence
<220> FEATURE:
<223> OTHER INFORMATION: Synthetic

<400> SEQUENCE: 68
taggcgatgc gcagcgcctg                                                    20

<210> SEQ ID NO 69
<211> LENGTH: 20
<212> TYPE: DNA
<213> ORGANISM: Artificial Sequence
<220> FEATURE:
<223> OTHER INFORMATION: Synthetic

<400> SEQUENCE: 69
caggcggtgc ggcacgcagt                                                    20

<210> SEQ ID NO 70
<211> LENGTH: 20
<212> TYPE: DNA
<213> ORGANISM: Artificial Sequence
<220> FEATURE:
<223> OTHER INFORMATION: Synthetic

<400> SEQUENCE: 70
ctgacgcctc ggctcgagct                                                    20

<210> SEQ ID NO 71
<211> LENGTH: 20
<212> TYPE: DNA
<213> ORGANISM: Artificial Sequence
<220> FEATURE:
<223> OTHER INFORMATION: Synthetic

<400> SEQUENCE: 71
attacgctgc gaaacgcagt                                                    20

<210> SEQ ID NO 72
<211> LENGTH: 20
<212> TYPE: DNA
<213> ORGANISM: Artificial Sequence
<220> FEATURE:
<223> OTHER INFORMATION: Synthetic

<400> SEQUENCE: 72
taatcggaac gtaacgatcc                                                    20

<210> SEQ ID NO 73
<211> LENGTH: 20
<212> TYPE: DNA
<213> ORGANISM: Artificial Sequence
<220> FEATURE:
<223> OTHER INFORMATION: Synthetic

<400> SEQUENCE: 73
catgcgtaac gttacggaaa                                                    20

<210> SEQ ID NO 74
<211> LENGTH: 11
<212> TYPE: DNA
```

<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(4)
<223> OTHER INFORMATION: n is a, c, g, or t
<220> FEATURE:
<221> NAME/KEY: misc_feature
<222> LOCATION: (7)..(9)
<223> OTHER INFORMATION: n is a, c, g, or t

<400> SEQUENCE: 74
cgnncgnnnc g         11

<210> SEQ ID NO 75
<211> LENGTH: 20
<212> TYPE: DNA
<213> ORGANISM: Artificial Sequence
<220> FEATURE:
<223> OTHER INFORMATION: Synthetic

<400> SEQUENCE: 75
ccagtcgggc ggggcgctgg         20

<210> SEQ ID NO 76
<211> LENGTH: 20
<212> TYPE: DNA
<213> ORGANISM: Artificial Sequence
<220> FEATURE:
<223> OTHER INFORMATION: Synthetic

<400> SEQUENCE: 76
gctggcgggc gaggcgattc         20

<210> SEQ ID NO 77
<211> LENGTH: 20
<212> TYPE: DNA
<213> ORGANISM: Artificial Sequence
<220> FEATURE:
<223> OTHER INFORMATION: Synthetic

<400> SEQUENCE: 77
accagcgggc gagtcgcctg         20

<210> SEQ ID NO 78
<211> LENGTH: 20
<212> TYPE: DNA
<213> ORGANISM: Artificial Sequence
<220> FEATURE:
<223> OTHER INFORMATION: Synthetic

<400> SEQUENCE: 78
ggtggcgggc gttgcgcatc         20

<210> SEQ ID NO 79
<211> LENGTH: 20
<212> TYPE: DNA
<213> ORGANISM: Artificial Sequence
<220> FEATURE:
<223> OTHER INFORMATION: Synthetic

<400> SEQUENCE: 79
ggcagcgggc gcatcgccag         20

<210> SEQ ID NO 80
<211> LENGTH: 20
<212> TYPE: DNA

-continued

```
<213> ORGANISM: Artificial Sequence
<220> FEATURE:
<223> OTHER INFORMATION: Synthetic

<400> SEQUENCE: 80
cttggcgggc gctgcgacca                                               20

<210> SEQ ID NO 81
<211> LENGTH: 20
<212> TYPE: DNA
<213> ORGANISM: Artificial Sequence
<220> FEATURE:
<223> OTHER INFORMATION: Synthetic

<400> SEQUENCE: 81
aactgcggac gtggcggcag                                               20

<210> SEQ ID NO 82
<211> LENGTH: 20
<212> TYPE: DNA
<213> ORGANISM: Artificial Sequence
<220> FEATURE:
<223> OTHER INFORMATION: Synthetic

<400> SEQUENCE: 82
ggtcacggtc ggatcgattc                                               20

<210> SEQ ID NO 83
<211> LENGTH: 20
<212> TYPE: DNA
<213> ORGANISM: Artificial Sequence
<220> FEATURE:
<223> OTHER INFORMATION: Synthetic

<400> SEQUENCE: 83
tttggcggtc ggtgcgcagc                                               20

<210> SEQ ID NO 84
<211> LENGTH: 20
<212> TYPE: DNA
<213> ORGANISM: Artificial Sequence
<220> FEATURE:
<223> OTHER INFORMATION: Synthetic

<400> SEQUENCE: 84
ggtggcggtc gaggcgctct                                               20

<210> SEQ ID NO 85
<211> LENGTH: 20
<212> TYPE: DNA
<213> ORGANISM: Artificial Sequence
<220> FEATURE:
<223> OTHER INFORMATION: Synthetic

<400> SEQUENCE: 85
ggtggcggtc gaggcgctct                                               20

<210> SEQ ID NO 86
<211> LENGTH: 20
<212> TYPE: DNA
<213> ORGANISM: Artificial Sequence
<220> FEATURE:
<223> OTHER INFORMATION: Synthetic

<400> SEQUENCE: 86
tttgtcggtc gcaacgaaaa                                               20
```

<210> SEQ ID NO 87
<211> LENGTH: 20
<212> TYPE: DNA
<213> ORGANISM: Artificial Sequence
<220> FEATURE:
<223> OTHER INFORMATION: Synthetic

<400> SEQUENCE: 87
gatgtcgagc ggatcggcac                                                  20

<210> SEQ ID NO 88
<211> LENGTH: 20
<212> TYPE: DNA
<213> ORGANISM: Artificial Sequence
<220> FEATURE:
<223> OTHER INFORMATION: Synthetic

<400> SEQUENCE: 88
ttgctcgagc ggttcggcat                                                  20

<210> SEQ ID NO 89
<211> LENGTH: 20
<212> TYPE: DNA
<213> ORGANISM: Artificial Sequence
<220> FEATURE:
<223> OTHER INFORMATION: Synthetic

<400> SEQUENCE: 89
ttggtcgagc gtgtcgggtg                                                  20

<210> SEQ ID NO 90
<211> LENGTH: 20
<212> TYPE: DNA
<213> ORGANISM: Artificial Sequence
<220> FEATURE:
<223> OTHER INFORMATION: Synthetic

<400> SEQUENCE: 90
agcatcgagc gcagcgtggt                                                  20

<210> SEQ ID NO 91
<211> LENGTH: 20
<212> TYPE: DNA
<213> ORGANISM: Artificial Sequence
<220> FEATURE:
<223> OTHER INFORMATION: Synthetic

<400> SEQUENCE: 91
ggcagcgagc gcaacgacac                                                  20

<210> SEQ ID NO 92
<211> LENGTH: 20
<212> TYPE: DNA
<213> ORGANISM: Artificial Sequence
<220> FEATURE:
<223> OTHER INFORMATION: Synthetic

<400> SEQUENCE: 92
ctcatcgagc gccacggcag                                                  20

<210> SEQ ID NO 93
<211> LENGTH: 20
<212> TYPE: DNA
<213> ORGANISM: Artificial Sequence
<220> FEATURE:
<223> OTHER INFORMATION: Synthetic

```
<400> SEQUENCE: 93
atgctcgagc gcctcggccc                                              20

<210> SEQ ID NO 94
<211> LENGTH: 20
<212> TYPE: DNA
<213> ORGANISM: Artificial Sequence
<220> FEATURE:
<223> OTHER INFORMATION: Synthetic

<400> SEQUENCE: 94
ggcttcgaac gggtcgaggg                                              20

<210> SEQ ID NO 95
<211> LENGTH: 20
<212> TYPE: DNA
<213> ORGANISM: Artificial Sequence
<220> FEATURE:
<223> OTHER INFORMATION: Synthetic

<400> SEQUENCE: 95
gatggcgaac gtgacgtcat                                              20

<210> SEQ ID NO 96
<211> LENGTH: 20
<212> TYPE: DNA
<213> ORGANISM: Artificial Sequence
<220> FEATURE:
<223> OTHER INFORMATION: Synthetic

<400> SEQUENCE: 96
cttgtcgaac gtctcggcca                                              20

<210> SEQ ID NO 97
<211> LENGTH: 20
<212> TYPE: DNA
<213> ORGANISM: Artificial Sequence
<220> FEATURE:
<223> OTHER INFORMATION: Synthetic

<400> SEQUENCE: 97
gagatcgaac gcttcgacac                                              20

<210> SEQ ID NO 98
<211> LENGTH: 20
<212> TYPE: DNA
<213> ORGANISM: Artificial Sequence
<220> FEATURE:
<223> OTHER INFORMATION: Synthetic

<400> SEQUENCE: 98
cagttcgatc gagacgaccc                                              20

<210> SEQ ID NO 99
<211> LENGTH: 20
<212> TYPE: DNA
<213> ORGANISM: Artificial Sequence
<220> FEATURE:
<223> OTHER INFORMATION: Synthetic

<400> SEQUENCE: 99
gtaggcgatc gatgcgccaa                                              20

<210> SEQ ID NO 100
<211> LENGTH: 20
<212> TYPE: DNA
```

```
<213> ORGANISM: Artificial Sequence
<220> FEATURE:
<223> OTHER INFORMATION: Synthetic

<400> SEQUENCE: 100
caacacgatc gtgtcggctg                                               20

<210> SEQ ID NO 101
<211> LENGTH: 20
<212> TYPE: DNA
<213> ORGANISM: Artificial Sequence
<220> FEATURE:
<223> OTHER INFORMATION: Synthetic

<400> SEQUENCE: 101
ctaggcgatc gcaacgaagt                                               20

<210> SEQ ID NO 102
<211> LENGTH: 20
<212> TYPE: DNA
<213> ORGANISM: Artificial Sequence
<220> FEATURE:
<223> OTHER INFORMATION: Synthetic

<400> SEQUENCE: 102
ccacacgatc gccacggtgg                                               20

<210> SEQ ID NO 103
<211> LENGTH: 20
<212> TYPE: DNA
<213> ORGANISM: Artificial Sequence
<220> FEATURE:
<223> OTHER INFORMATION: Synthetic

<400> SEQUENCE: 103
ggcagcgtgc gtgacgactt                                               20

<210> SEQ ID NO 104
<211> LENGTH: 20
<212> TYPE: DNA
<213> ORGANISM: Artificial Sequence
<220> FEATURE:
<223> OTHER INFORMATION: Synthetic

<400> SEQUENCE: 104
taaggcgtgc gcatcgatat                                               20

<210> SEQ ID NO 105
<211> LENGTH: 20
<212> TYPE: DNA
<213> ORGANISM: Artificial Sequence
<220> FEATURE:
<223> OTHER INFORMATION: Synthetic

<400> SEQUENCE: 105
agcagcgttc gtgtcggcct                                               20

<210> SEQ ID NO 106
<211> LENGTH: 20
<212> TYPE: DNA
<213> ORGANISM: Artificial Sequence
<220> FEATURE:
<223> OTHER INFORMATION: Synthetic

<400> SEQUENCE: 106
tgttgcgcac ggtgcgctgc                                               20
```

```
<210> SEQ ID NO 107
<211> LENGTH: 20
<212> TYPE: DNA
<213> ORGANISM: Artificial Sequence
<220> FEATURE:
<223> OTHER INFORMATION: Synthetic

<400> SEQUENCE: 107
ctgggcgcac ggcacgctgg                                              20

<210> SEQ ID NO 108
<211> LENGTH: 20
<212> TYPE: DNA
<213> ORGANISM: Artificial Sequence
<220> FEATURE:
<223> OTHER INFORMATION: Synthetic

<400> SEQUENCE: 108
ggcagcgcac gcagcgcaac                                              20

<210> SEQ ID NO 109
<211> LENGTH: 20
<212> TYPE: DNA
<213> ORGANISM: Artificial Sequence
<220> FEATURE:
<223> OTHER INFORMATION: Synthetic

<400> SEQUENCE: 109
gcaggcgctc gtcacgcccc                                              20

<210> SEQ ID NO 110
<211> LENGTH: 12
<212> TYPE: DNA
<213> ORGANISM: Artificial Sequence
<220> FEATURE:
<223> OTHER INFORMATION: Synthetic
<220> FEATURE:
<221> NAME/KEY: misc_feature
<222> LOCATION: (3)..(5)
<223> OTHER INFORMATION: n is a, c, g, or t
<220> FEATURE:
<221> NAME/KEY: misc_feature
<222> LOCATION: (8)..(10)
<223> OTHER INFORMATION: n is a, c, g, or t

<400> SEQUENCE: 110
cgnnncgnnn cg                                                      12

<210> SEQ ID NO 111
<211> LENGTH: 20
<212> TYPE: DNA
<213> ORGANISM: Artificial Sequence
<220> FEATURE:
<223> OTHER INFORMATION: Synthetic

<400> SEQUENCE: 111
gatgcggatc ggtgcgctgc                                              20

<210> SEQ ID NO 112
<211> LENGTH: 20
<212> TYPE: DNA
<213> ORGANISM: Artificial Sequence
<220> FEATURE:
<223> OTHER INFORMATION: Synthetic

<400> SEQUENCE: 112
caggcggtgc gcaacgcctg                                              20
```

<210> SEQ ID NO 113
<211> LENGTH: 20
<212> TYPE: DNA
<213> ORGANISM: Artificial Sequence
<220> FEATURE:
<223> OTHER INFORMATION: Synthetic

<400> SEQUENCE: 113
gatgcggtgc gcatcgccaa                                               20

<210> SEQ ID NO 114
<211> LENGTH: 20
<212> TYPE: DNA
<213> ORGANISM: Artificial Sequence
<220> FEATURE:
<223> OTHER INFORMATION: Synthetic

<400> SEQUENCE: 114
gaggcggtgc gccacgtgct                                               20

<210> SEQ ID NO 115
<211> LENGTH: 20
<212> TYPE: DNA
<213> ORGANISM: Artificial Sequence
<220> FEATURE:
<223> OTHER INFORMATION: Synthetic

<400> SEQUENCE: 115
ggagcggctc gacacgacaa                                               20

<210> SEQ ID NO 116
<211> LENGTH: 20
<212> TYPE: DNA
<213> ORGANISM: Artificial Sequence
<220> FEATURE:
<223> OTHER INFORMATION: Synthetic

<400> SEQUENCE: 116
tggtcgaggc gttgcgggac                                               20

<210> SEQ ID NO 117
<211> LENGTH: 20
<212> TYPE: DNA
<213> ORGANISM: Artificial Sequence
<220> FEATURE:
<223> OTHER INFORMATION: Synthetic

<400> SEQUENCE: 117
acagcgagtc gctgcgccac                                               20

<210> SEQ ID NO 118
<211> LENGTH: 20
<212> TYPE: DNA
<213> ORGANISM: Artificial Sequence
<220> FEATURE:
<223> OTHER INFORMATION: Synthetic

<400> SEQUENCE: 118
taggcgaagc gatgcggccc                                               20

<210> SEQ ID NO 119
<211> LENGTH: 20
<212> TYPE: DNA
<213> ORGANISM: Artificial Sequence
<220> FEATURE:
<223> OTHER INFORMATION: Synthetic

```
<400> SEQUENCE: 119
tcagcgaagc ggtgcgccca                                               20

<210> SEQ ID NO 120
<211> LENGTH: 20
<212> TYPE: DNA
<213> ORGANISM: Artificial Sequence
<220> FEATURE:
<223> OTHER INFORMATION: Synthetic

<400> SEQUENCE: 120
atctcgaagc gctgcgaggg                                               20

<210> SEQ ID NO 121
<211> LENGTH: 20
<212> TYPE: DNA
<213> ORGANISM: Artificial Sequence
<220> FEATURE:
<223> OTHER INFORMATION: Synthetic

<400> SEQUENCE: 121
gggtcgaatc gtgtcgcctc                                               20

<210> SEQ ID NO 122
<211> LENGTH: 20
<212> TYPE: DNA
<213> ORGANISM: Artificial Sequence
<220> FEATURE:
<223> OTHER INFORMATION: Synthetic

<400> SEQUENCE: 122
taggcgatgc gcagcgcctg                                               20

<210> SEQ ID NO 123
<211> LENGTH: 20
<212> TYPE: DNA
<213> ORGANISM: Artificial Sequence
<220> FEATURE:
<223> OTHER INFORMATION: Synthetic

<400> SEQUENCE: 123
atggcgatgc gctgcgcctg                                               20

<210> SEQ ID NO 124
<211> LENGTH: 20
<212> TYPE: DNA
<213> ORGANISM: Artificial Sequence
<220> FEATURE:
<223> OTHER INFORMATION: Synthetic

<400> SEQUENCE: 124
gggtcgacac gctgcgattg                                               20

<210> SEQ ID NO 125
<211> LENGTH: 20
<212> TYPE: DNA
<213> ORGANISM: Artificial Sequence
<220> FEATURE:
<223> OTHER INFORMATION: Synthetic

<400> SEQUENCE: 125
tgctcgtggc ggctcggcag                                               20

<210> SEQ ID NO 126
<211> LENGTH: 20
<212> TYPE: DNA
```

<213> ORGANISM: Artificial Sequence
<220> FEATURE:
<223> OTHER INFORMATION: Synthetic

<400> SEQUENCE: 126
ccagcgtggc gatgcgggca                                           20

<210> SEQ ID NO 127
<211> LENGTH: 20
<212> TYPE: DNA
<213> ORGANISM: Artificial Sequence
<220> FEATURE:
<223> OTHER INFORMATION: Synthetic

<400> SEQUENCE: 127
gcatcgtggc gcagcgcatg                                           20

<210> SEQ ID NO 128
<211> LENGTH: 20
<212> TYPE: DNA
<213> ORGANISM: Artificial Sequence
<220> FEATURE:
<223> OTHER INFORMATION: Synthetic

<400> SEQUENCE: 128
tggacgtgtc gtagcgcagg                                           20

<210> SEQ ID NO 129
<211> LENGTH: 20
<212> TYPE: DNA
<213> ORGANISM: Artificial Sequence
<220> FEATURE:
<223> OTHER INFORMATION: Synthetic

<400> SEQUENCE: 129
ctggcgtagc gcctcggcct                                           20

<210> SEQ ID NO 130
<211> LENGTH: 20
<212> TYPE: DNA
<213> ORGANISM: Artificial Sequence
<220> FEATURE:
<223> OTHER INFORMATION: Synthetic

<400> SEQUENCE: 130
ttggcgttgc gtgtcggcct                                           20

<210> SEQ ID NO 131
<211> LENGTH: 20
<212> TYPE: DNA
<213> ORGANISM: Artificial Sequence
<220> FEATURE:
<223> OTHER INFORMATION: Synthetic

<400> SEQUENCE: 131
aaatcgttgc ggcacggcat                                           20

<210> SEQ ID NO 132
<211> LENGTH: 20
<212> TYPE: DNA
<213> ORGANISM: Artificial Sequence
<220> FEATURE:
<223> OTHER INFORMATION: Synthetic

<400> SEQUENCE: 132
atcacgttgc gcagcgggtg                                           20

```
<210> SEQ ID NO 133
<211> LENGTH: 20
<212> TYPE: DNA
<213> ORGANISM: Artificial Sequence
<220> FEATURE:
<223> OTHER INFORMATION: Synthetic

<400> SEQUENCE: 133
aaatcgtctc gaggcgttcc                                              20

<210> SEQ ID NO 134
<211> LENGTH: 20
<212> TYPE: DNA
<213> ORGANISM: Artificial Sequence
<220> FEATURE:
<223> OTHER INFORMATION: Synthetic

<400> SEQUENCE: 134
gtggcgcagc gtggcggtgg                                              20

<210> SEQ ID NO 135
<211> LENGTH: 20
<212> TYPE: DNA
<213> ORGANISM: Artificial Sequence
<220> FEATURE:
<223> OTHER INFORMATION: Synthetic

<400> SEQUENCE: 135
tgggcgcagc ggcacgctat                                              20

<210> SEQ ID NO 136
<211> LENGTH: 20
<212> TYPE: DNA
<213> ORGANISM: Artificial Sequence
<220> FEATURE:
<223> OTHER INFORMATION: Synthetic

<400> SEQUENCE: 136
tctgcgcagc gcatcgttga                                              20

<210> SEQ ID NO 137
<211> LENGTH: 20
<212> TYPE: DNA
<213> ORGANISM: Artificial Sequence
<220> FEATURE:
<223> OTHER INFORMATION: Synthetic

<400> SEQUENCE: 137
tgggcgcagc gttacgaact                                              20

<210> SEQ ID NO 138
<211> LENGTH: 20
<212> TYPE: DNA
<213> ORGANISM: Artificial Sequence
<220> FEATURE:
<223> OTHER INFORMATION: Synthetic

<400> SEQUENCE: 138
gcctcgcagc gacacgttgg                                              20

<210> SEQ ID NO 139
<211> LENGTH: 20
<212> TYPE: DNA
<213> ORGANISM: Artificial Sequence
<220> FEATURE:
<223> OTHER INFORMATION: Synthetic
```

-continued

<400> SEQUENCE: 139
ttggcgcaac gcatcggaga					20

<210> SEQ ID NO 140
<211> LENGTH: 20
<212> TYPE: DNA
<213> ORGANISM: Artificial Sequence
<220> FEATURE:
<223> OTHER INFORMATION: Synthetic

<400> SEQUENCE: 140
ggagcgcaac gttgcgcatc					20

<210> SEQ ID NO 141
<211> LENGTH: 20
<212> TYPE: DNA
<213> ORGANISM: Artificial Sequence
<220> FEATURE:
<223> OTHER INFORMATION: Synthetic

<400> SEQUENCE: 141
acaacgcatc gcatcgagga					20

<210> SEQ ID NO 142
<211> LENGTH: 20
<212> TYPE: DNA
<213> ORGANISM: Artificial Sequence
<220> FEATURE:
<223> OTHER INFORMATION: Synthetic

<400> SEQUENCE: 142
agcacgctgc gggtcgtcag					20

<210> SEQ ID NO 143
<211> LENGTH: 20
<212> TYPE: DNA
<213> ORGANISM: Artificial Sequence
<220> FEATURE:
<223> OTHER INFORMATION: Synthetic

<400> SEQUENCE: 143
actgcgctgc ggcacgaccc					20

<210> SEQ ID NO 144
<211> LENGTH: 20
<212> TYPE: DNA
<213> ORGANISM: Artificial Sequence
<220> FEATURE:
<223> OTHER INFORMATION: Synthetic

<400> SEQUENCE: 144
gtctcgctgc gcagcggggt					20

<210> SEQ ID NO 145
<211> LENGTH: 20
<212> TYPE: DNA
<213> ORGANISM: Artificial Sequence
<220> FEATURE:
<223> OTHER INFORMATION: Synthetic

<400> SEQUENCE: 145
gggacgctgc gtgacgtggt					20

<210> SEQ ID NO 146
<211> LENGTH: 20
<212> TYPE: DNA

```
<213> ORGANISM: Artificial Sequence
<220> FEATURE:
<223> OTHER INFORMATION: Synthetic

<400> SEQUENCE: 146
ctgacgcctc ggctcgagct                                                     20

<210> SEQ ID NO 147
<211> LENGTH: 20
<212> TYPE: DNA
<213> ORGANISM: Artificial Sequence
<220> FEATURE:
<223> OTHER INFORMATION: Synthetic

<400> SEQUENCE: 147
agcagcgttc gtgtcggcct                                                     20

<210> SEQ ID NO 148
<211> LENGTH: 20
<212> TYPE: DNA
<213> ORGANISM: Artificial Sequence
<220> FEATURE:
<223> OTHER INFORMATION: Synthetic

<400> SEQUENCE: 148
cagctcgttc gtgtcgtgct                                                     20

<210> SEQ ID NO 149
<211> LENGTH: 20
<212> TYPE: DNA
<213> ORGANISM: Artificial Sequence
<220> FEATURE:
<223> OTHER INFORMATION: Synthetic

<400> SEQUENCE: 149
tgtggcgttc gtgtcggtct                                                     20

<210> SEQ ID NO 150
<211> LENGTH: 20
<212> TYPE: DNA
<213> ORGANISM: Artificial Sequence
<220> FEATURE:
<223> OTHER INFORMATION: Synthetic

<400> SEQUENCE: 150
tgcaacgttc gtgtcgccac                                                     20

<210> SEQ ID NO 151
<211> LENGTH: 20
<212> TYPE: DNA
<213> ORGANISM: Artificial Sequence
<220> FEATURE:
<223> OTHER INFORMATION: Synthetic

<400> SEQUENCE: 151
ggccacgttc gtgtcggtag                                                     20

<210> SEQ ID NO 152
<211> LENGTH: 20
<212> TYPE: DNA
<213> ORGANISM: Artificial Sequence
<220> FEATURE:
<223> OTHER INFORMATION: Synthetic

<400> SEQUENCE: 152
gaacacgttc gtgtcggaac                                                     20
```

```
<210> SEQ ID NO 153
<211> LENGTH: 20
<212> TYPE: DNA
<213> ORGANISM: Artificial Sequence
<220> FEATURE:
<223> OTHER INFORMATION: Synthetic

<400> SEQUENCE: 153
cagcacgttc gtgtcggaca                                                    20

<210> SEQ ID NO 154
<211> LENGTH: 20
<212> TYPE: DNA
<213> ORGANISM: Artificial Sequence
<220> FEATURE:
<223> OTHER INFORMATION: Synthetic

<400> SEQUENCE: 154
tatgtcgttc gtgtcgtctt                                                    20

<210> SEQ ID NO 155
<211> LENGTH: 20
<212> TYPE: DNA
<213> ORGANISM: Artificial Sequence
<220> FEATURE:
<223> OTHER INFORMATION: Synthetic

<400> SEQUENCE: 155
aagggcgttc gtgtcgcttg                                                    20

<210> SEQ ID NO 156
<211> LENGTH: 20
<212> TYPE: DNA
<213> ORGANISM: Artificial Sequence
<220> FEATURE:
<223> OTHER INFORMATION: Synthetic

<400> SEQUENCE: 156
atttgcgttc gtgtcgattc                                                    20

<210> SEQ ID NO 157
<211> LENGTH: 20
<212> TYPE: DNA
<213> ORGANISM: Artificial Sequence
<220> FEATURE:
<223> OTHER INFORMATION: Synthetic

<400> SEQUENCE: 157
ggtggcgttc gtgtcgtcat                                                    20

<210> SEQ ID NO 158
<211> LENGTH: 20
<212> TYPE: DNA
<213> ORGANISM: Artificial Sequence
<220> FEATURE:
<223> OTHER INFORMATION: Synthetic

<400> SEQUENCE: 158
atgggcgttc gtgtcgatcc                                                    20

<210> SEQ ID NO 159
<211> LENGTH: 20
<212> TYPE: DNA
<213> ORGANISM: Artificial Sequence
<220> FEATURE:
<223> OTHER INFORMATION: Synthetic
```

```
<400> SEQUENCE: 159
gtattcgttc gtgtcgtcct                                              20

<210> SEQ ID NO 160
<211> LENGTH: 20
<212> TYPE: DNA
<213> ORGANISM: Artificial Sequence
<220> FEATURE:
<223> OTHER INFORMATION: Synthetic

<400> SEQUENCE: 160
gggaacgttc gtgtcggtgc                                              20

<210> SEQ ID NO 161
<211> LENGTH: 20
<212> TYPE: DNA
<213> ORGANISM: Artificial Sequence
<220> FEATURE:
<223> OTHER INFORMATION: Synthetic

<400> SEQUENCE: 161
tgactcgttc gtgtcgcatg                                              20

<210> SEQ ID NO 162
<211> LENGTH: 20
<212> TYPE: DNA
<213> ORGANISM: Artificial Sequence
<220> FEATURE:
<223> OTHER INFORMATION: Synthetic

<400> SEQUENCE: 162
gtcatcgttc gtgtcgagac                                              20

<210> SEQ ID NO 163
<211> LENGTH: 20
<212> TYPE: DNA
<213> ORGANISM: Artificial Sequence
<220> FEATURE:
<223> OTHER INFORMATION: Synthetic

<400> SEQUENCE: 163
ttgcacgttc gtgtcgatga                                              20

<210> SEQ ID NO 164
<211> LENGTH: 20
<212> TYPE: DNA
<213> ORGANISM: Artificial Sequence
<220> FEATURE:
<223> OTHER INFORMATION: Synthetic

<400> SEQUENCE: 164
cagcacgttc gtgtcggtca                                              20

<210> SEQ ID NO 165
<211> LENGTH: 20
<212> TYPE: DNA
<213> ORGANISM: Artificial Sequence
<220> FEATURE:
<223> OTHER INFORMATION: Synthetic

<400> SEQUENCE: 165
agcagcgttc gtgtcggcct                                              20

<210> SEQ ID NO 166
<211> LENGTH: 15
<212> TYPE: DNA
```

<213> ORGANISM: Artificial Sequence
<220> FEATURE:
<223> OTHER INFORMATION: Synthetic

<400> SEQUENCE: 166
agcgttcgtg tcggc                                                    15

<210> SEQ ID NO 167
<211> LENGTH: 20
<212> TYPE: DNA
<213> ORGANISM: Artificial Sequence
<220> FEATURE:
<223> OTHER INFORMATION: Synthetic

<400> SEQUENCE: 167
agcaggcttc gtgtcggcct                                               20

<210> SEQ ID NO 168
<211> LENGTH: 20
<212> TYPE: DNA
<213> ORGANISM: Artificial Sequence
<220> FEATURE:
<223> OTHER INFORMATION: Synthetic

<400> SEQUENCE: 168
agcagcgttg ctgtcggcct                                               20

<210> SEQ ID NO 169
<211> LENGTH: 20
<212> TYPE: DNA
<213> ORGANISM: Artificial Sequence
<220> FEATURE:
<223> OTHER INFORMATION: Synthetic

<400> SEQUENCE: 169
agcagcgttc gtgtgcgcct                                               20

<210> SEQ ID NO 170
<211> LENGTH: 20
<212> TYPE: DNA
<213> ORGANISM: Artificial Sequence
<220> FEATURE:
<223> OTHER INFORMATION: Synthetic

<400> SEQUENCE: 170
agcaggcttg ctgtcggcct                                               20

<210> SEQ ID NO 171
<211> LENGTH: 20
<212> TYPE: DNA
<213> ORGANISM: Artificial Sequence
<220> FEATURE:
<223> OTHER INFORMATION: Synthetic

<400> SEQUENCE: 171
agcaggcttc gtgtgcgcct                                               20

<210> SEQ ID NO 172
<211> LENGTH: 20
<212> TYPE: DNA
<213> ORGANISM: Artificial Sequence
<220> FEATURE:
<223> OTHER INFORMATION: Synthetic

<400> SEQUENCE: 172
agcagcgttg ctgtgcgcct                                               20

<210> SEQ ID NO 173
<211> LENGTH: 20
<212> TYPE: DNA
<213> ORGANISM: Artificial Sequence
<220> FEATURE:
<223> OTHER INFORMATION: Synthetic

<400> SEQUENCE: 173
agcaggcttg ctgtgcgcct                                                    20

<210> SEQ ID NO 174
<211> LENGTH: 20
<212> TYPE: DNA
<213> ORGANISM: Artificial Sequence
<220> FEATURE:
<223> OTHER INFORMATION: Synthetic

<400> SEQUENCE: 174
agcagcattc gtgtcggcct                                                    20

<210> SEQ ID NO 175
<211> LENGTH: 20
<212> TYPE: DNA
<213> ORGANISM: Artificial Sequence
<220> FEATURE:
<223> OTHER INFORMATION: Synthetic

<400> SEQUENCE: 175
agcagctttc gtgtcggcct                                                    20

<210> SEQ ID NO 176
<211> LENGTH: 20
<212> TYPE: DNA
<213> ORGANISM: Artificial Sequence
<220> FEATURE:
<223> OTHER INFORMATION: Synthetic

<400> SEQUENCE: 176
agcagccttc gtgtcggcct                                                    20

<210> SEQ ID NO 177
<211> LENGTH: 20
<212> TYPE: DNA
<213> ORGANISM: Artificial Sequence
<220> FEATURE:
<223> OTHER INFORMATION: Synthetic

<400> SEQUENCE: 177
agcagcgttc atgtcggcct                                                    20

<210> SEQ ID NO 178
<211> LENGTH: 20
<212> TYPE: DNA
<213> ORGANISM: Artificial Sequence
<220> FEATURE:
<223> OTHER INFORMATION: Synthetic

<400> SEQUENCE: 178
agcagcgttc ttgtcggcct                                                    20

<210> SEQ ID NO 179
<211> LENGTH: 20
<212> TYPE: DNA
<213> ORGANISM: Artificial Sequence
<220> FEATURE:
<223> OTHER INFORMATION: Synthetic

```
<400> SEQUENCE: 179
agcagcgttc ctgtcggcct                                                    20

<210> SEQ ID NO 180
<211> LENGTH: 20
<212> TYPE: DNA
<213> ORGANISM: Artificial Sequence
<220> FEATURE:
<223> OTHER INFORMATION: Synthetic

<400> SEQUENCE: 180
agcagcgttc gtgtcagcct                                                    20

<210> SEQ ID NO 181
<211> LENGTH: 20
<212> TYPE: DNA
<213> ORGANISM: Artificial Sequence
<220> FEATURE:
<223> OTHER INFORMATION: Synthetic

<400> SEQUENCE: 181
agcagcgttc gtgtctgcct                                                    20

<210> SEQ ID NO 182
<211> LENGTH: 20
<212> TYPE: DNA
<213> ORGANISM: Artificial Sequence
<220> FEATURE:
<223> OTHER INFORMATION: Synthetic

<400> SEQUENCE: 182
agcagcgttc gtgtccgcct                                                    20

<210> SEQ ID NO 183
<211> LENGTH: 20
<212> TYPE: DNA
<213> ORGANISM: Artificial Sequence
<220> FEATURE:
<223> OTHER INFORMATION: Synthetic

<400> SEQUENCE: 183
agcagcattc atgtcggcct                                                    20

<210> SEQ ID NO 184
<211> LENGTH: 20
<212> TYPE: DNA
<213> ORGANISM: Artificial Sequence
<220> FEATURE:
<223> OTHER INFORMATION: Synthetic

<400> SEQUENCE: 184
agcagcattc gtgtcagcct                                                    20

<210> SEQ ID NO 185
<211> LENGTH: 20
<212> TYPE: DNA
<213> ORGANISM: Artificial Sequence
<220> FEATURE:
<223> OTHER INFORMATION: Synthetic

<400> SEQUENCE: 185
agcagcgttc atgtcagcct                                                    20

<210> SEQ ID NO 186
<211> LENGTH: 11
<212> TYPE: DNA
```

```
<213> ORGANISM: Artificial Sequence
<220> FEATURE:
<223> OTHER INFORMATION: Synthetic

<400> SEQUENCE: 186
cgttcgtgtc g                                                      11

<210> SEQ ID NO 187
<211> LENGTH: 20
<212> TYPE: DNA
<213> ORGANISM: Artificial Sequence
<220> FEATURE:
<223> OTHER INFORMATION: Synthetic

<400> SEQUENCE: 187
gacgttgagt cgttaacgag                                             20
```

OLIGONUCLEOTIDES DERIVED FROM *MYCOBACTERIUM* FOR STIMULATING IMMUNE FUNCTION, TREATING IMMUNE-RELATED DISEASES, ATOPIC DERMATITIS AND/OR PROTECTING NORMAL IMMUNE CELL

TECHNICAL FIELD

The present invention relates to oligonucleotides derived from *Mycobacterium* for manipulating immune reactions, which may stimulate immune reactions and maintain a balance of the immune reactions and have an effect on various immune-related diseases such as an atopic dermatitis, etc. in terms of a therapeutic use, and more specifically to oligonucleotides having three CpG motifs involved in stimulating immune reactions, which have an efficacy that is varied according to modification of the DNA sequence(s), and may be used in treatment of various immune-related diseases- and an atopic dermatitis by stimulating immune reactions (an adjuvant) by the oligodeoxynucleotides in the form of phosphodiester and maintaining a balance of the Th1/Th2 immune reactions, and also have an effect of increasing viability of the cells as a treatment of the radiation.

BACKGROUND ART

An immune system, generally initiated through an innate immune system, should be elaborately controlled to keep its balance. That is, the balances between immunity and tolerance, between T helper type 1 (Th1) and T helper type 2 (Th2) immunities, and between inflammation and unresponsiveness should be necessarily controlled elaborately. Unfortunately, conditions such as autoimmune-related diseases, allergic diseases, chronic inflammation, etc. have, however, been spread since many therapeutic agents for the immune-related diseases developed up to now could not control the immune system adequately. However, the innate immune system is a mechanism in which immune cells are activated by recognizing a structural difference of a foreign substance (Pathogen-Associated Molecular Pattern, PAMP) when a pathogen was invaded, and subsequent signals are transmitted to initiate a cascade reaction of the immune system, resulting in destruction of the pathogen. Accordingly, therapeutic agents of the immune-related diseases should be necessarily developed to minimize the Evil mechanism after exact understanding of a Good & Evil mechanism using the innate immune system.

In the 1890's, William B. Coley observed a surprising result that infection of pathogenic microorganisms may induce an anti-cancer effect in cancer patients, and therefore it was found that its modified bacterial therapy has about 40% of the therapeutic effect if it is subject to 900 cancer patients. In the 1980's, Japanese researchers recognized utility of Coley's toxin in a different and new aspect, proved that an active fraction of *Bacillus* Calmette-Guerin (BCG) shows an anti-cancer effect, and confirmed that the anti-cancer activity of BCG is derived from an inherent characteristics of DNA sequence. In 1995, Kreig, et al. proved, during the study of antisense oligonucleotides suppressing genes of a B cell, the fact that a synthetic oligodeoxynucleotides (ODNs) of a specific DNA sequence composed of unmethylated cytosine and guanine may induce activation of the immune cells. From the Kreig's aspect, it was newly presented that the anti-cancer effect of BCG proved by the Japanese researchers in the art is derived from the characteristics of unmethylated BCG DNA, and the immunological activation by such a bacterial DNA allows the immune system of the vertebrate to distinguish self DNA and non-self DNA.

The early studies of the immunological activation and its control by bacteria focused on protein antigens such as Coley's toxin, which induces generation of the antibody. However, many of the studies reported that more powerful inducers for the immunological activation are present among the components of the microorganism. And, it was also proved that the bacterial DNA is prone to induce a powerful immunological activation, and certain immune responses to each antigen (6, 7). An CpG dinucleotide composed of two nucleic acid sequences is a gist, of the immunological activation and its control, and it was revealed from the recent studies that the vertebrate also distinguishes self DNA from bacterial DNA to activate the immune cells. Such a CpG motif is plentiful in the bacteria, but not in the vertebrate. It was seen that an oligodeoxynucleotide including the CpG motifs (CpG-oligodeoxynucleotide, CpG-ODN) activates various defense mechanisms of the host including innate immune responses and acquired immune responses (Akdis, C A. *Curr Opin Immunol.*, 12:641-646, 2000).

Recently, there has been developed a CpG-ODN whose backbone was modified so as to increase usability of the CpG-ODN. The CpG-ODN with a phosphodiester backbone referred to as a basic backbone of DNA, was easily decomposed in the body since it was sensitive to nucleases. Accordingly, the CpG-ODN has a low risk of inducing in vivo toxicity. However, it is revealed that the CpG-ODN with the phosphodiester backbone has a lower activity than the CpG-ODNs of the other backbones (Kwon, H J. et al., *Biochem. Biophys. Res. Commun.*, 311:129-138, 2003). On the other hand, the CpG-ODN with the phosphorothioate backbone was artificially engineered by modifying its structure so that it cannot be decomposed in vivo by the nuclease. The CpG-ODN with the phosphorothioate backbone has a good in vivo stability and an excellent ability to activate the B cells, compared to the CpG-ODN with the phosphodiester backbone. Accordingly, the CpG-ODN modified into the phosphorothioate backbone has been widely used lately. However, such a CpG-ODN with the phosphorothioate backbone induces toxicity since it increase binding by the ODN non-specific to many proteins, and therefore it is not easily decomposed in vivo. Also, it was reported that the CpG-ODN with the phosphorothioate backbone induces the arthritis and exacerbates its symptoms (Deng G M et al., *Arthritis & Rheumatism*, 43 (2): 356-364, 2000), and causes the autoimmune-related diseases such as SLE (systemic lupus erythematosis) (Tanaka, T. et al., *J Exp. Med.* 175:597-607, 1992).

Formulations has been manufactured by adding various materials as the adjuvant to vaccine, and such a formulation has been designed to maximize an effect of the vaccine since the event of this century. However, aluminum salt (alum, $Al_2O_3$) is now only an adjuvant approved so that it can be administered in the vaccine. In the recent study, it was found that efficacy of the vaccine was much more excellent when a recombinant hepatitis surface antigen was mixed with the alum and the CpG-ODN and administered to a mouse than when only the alum was used as the adjuvant (Davis H L. et al. J. Immunol. 160: 870-876, 1998). It was seen that the alum slightly induces cell-mediated immunity by inducing the Th2 immune reaction, while the CpG ODN strongly induces humoral and cell-mediated immunity by inducing expression of the Th1 cytokines. However, the problem is that the CpG-ODN used in this case may cause a side effect since it has a phosphorothioate backbone.

Meanwhile, skin diseases are referred to as all abnormalities that appear in the skin of the animals including human. Amongst them, an atopic dermatitis has characteristic major symptoms such as chronic/inflammatory skin diseases selected from the group consisting of a serious pruritus, dry skins and an eczematous dermatitis (Rudikoff, D. et al. *Lancet.* 351:1715-1721, 1998). Generally, the atopic dermatitis tends to be inherited, and accompanied by an allergic asthma, an allergic rhinitis, an allergic conjunctivitis and an urticaria, depending on individuals. A series of immunological abnormalities reported in the atopic dermatitis patients include an increased production of IgE, the reduced number and deteriorated function of CD8+ suppressor/cytotoxic T lymphocytes, the reduced number of Th1 (T-cell Helper type 1) lymphocyte that secretes IFN-gamma, etc. Also, T lymphocyte having histological CD4+ phenotype, infiltration of monocytes/macrophages, mast cells and eosinophils are increased in the skin abnormality of the atopic dermatitis, and dendritic cells (DCs) and epidermal Langerhans cells are also increased in the skin abnormality of the atopic dermatitis (Imokawa, G., et al., *J. Invest. Dermatol.*, 96:523-526, 1991).

Many researchers have developed the methods for treating the cancer by killing the cancer cells using X-ray. However, when the cancer is treated using the irradiation, cancer tissues and its adjacent immune cells all are inevitably damaged due to the irradiation, resulting in its reduced immune functions. It has been reported that the immune cells such as B cells (Ashwell J D et al., *J. Immunol.* 136:3649-3656, 1986), T cells (Prosser J S *Int. J. Radiat. Biol. Relat. Stud. Phys. Chem. Med.* 30:459-465, 1976), macrophages (Yoshihisa K et al., *J. Radiat Res.* 45:205-211, 2004), etc. were killed by the irradiation (apoptosis). Accordingly, among the radiotherapeutic methods for treating the diseases such as a cancer, etc., there are required the methods that normal immune cells except the cancerous cells are survived to normally maintain the immune reactions.

The present invention relates to oligonucleotides derived from *Mycobacterium bovis* BCG for manipulating immune reactions, which may be used in treatment of various immune-related diseases by stimulating immune reactions (an adjuvant) and maintaining a balance of the immune reactions, and also have effects of treating an atopic dermatitis and increasing viability of the cells as a function of the irradiation.

DISCLOSURE OF INVENTION

Accordingly, the present invention provides CpG oligodeoxynucleotides isolated from the *Mycobacterium bovis* BCG (MB-ODN), which are presented in following General Formula and composed of DNA sequences including at least two unmethylated CpG motifs, wherein the CpG oligodeoxynucleotides may be used to stimulate immune reactions (an adjuvant), maintain a balance of Th1/Th2 immune reactions so as to treat various immune-related diseases, and protect normal immune cells when intractable diseases such as a cancer, etc. are treated using the radiotherapy, and also provides a method for treating or preventing skin diseases.

[General Formula]: HKCGTTCRTGTCSGM     (SEQ ID NO: 1)

wherein, R represents A or G; S represents C or G; H represents A, T or C; K represents G or T; and M represents C or A.

In the present invention, the oligonucleotides preferably further include five nucleotides, presented in following General Formula, at a 5'-terminal end and a 3'-terminal end:

(SEQ ID NO: 2)
[General Formula]: DKMHKCGTTCRTGTCSGMYK wherein, R represents A or G; S represents C or G; H represents A, T or C; K represents G or T; D represents A, G or T; M represents C or A; M represents C or A; and Y represents C or T.

In the present invention, the term 'CpG motif' means a DNA sequence that includes unmethylated cytosine-guanine dinucleotides (referred to as unmethylated cytosine-phosphate-guanine dinucleotides) connected by phosphodiester bond (phosphate bond), and activates immune reactions. Also, the term 'CpG oligodeoxynucleotide (hereinafter, referred to as 'CpG-ODN')' means an oligodeoxynucleotide that includes at least two CpG motifs.

Also in the present invention, the term subject means a mammal, particularly an animal including human. The subject may be a patient in need of treatment.

In the present invention, the oligonucleotides is preferably selected from the group consisting of 5'-AGCAGCGTTCGT-GTCGGCCT-3' (SEQ ID NO: 3), 5'-AGCAGCGTTCGTGT-GCGCCT-3' (SEQ ID NO: 4), 5'-AGCAGCGTTCATGTCG-GCCT-3' (SEQ ID NO: 5), 5'-AGCAGCGTTCGTGTCCGCCT-3' (SEQ ID NO: 6), 5'-GTATTCGTTCGTGTCGTCCT-3' (SEQ ID NO: 7), and 5'-TGACTCGTTCGTGTCGCATG-3' (SEQ ID NO: 8).

The MB-ODN of the present invention may be derived from natural sources (for example, chromosomal DNA of *M. bovis* BCG), and chemically synthesized, or recombinantly manufactured. The MB-ODN of the present invention may be synthesized using various techniques and apparatuses for synthesizing the nucleic acid, known in the art (Ausubel et al., *Current Protocols in Molecular Biology*, Chs 2, and 4 (Wiley Interscience, 1989); Maniatis, et al., Molecular Cloning: *A Laboratory Manual* (Cold Spring Harbor Lab., New York, 1982); and U.S. Pat. No. 4,458,066).

The MB-ODN of the present invention preferably has a phosphodiester backbone. The phosphodiester backbone, referred to as a basic backbone of DNA, has a low risk of inducing in vivo toxicity since it is easily decomposed in vivo by the nucleases. The MB-ODN of the present invention is characterized in that it has an excellent immunological activity in vitro and in vivo unlike the other conventional CpG ODNs although it has the phosphodiester backbone. Also, the MB-ODN of the present invention may include modified backbones. It was revealed that modification of the oligonucleotide backbone might allow the CpG ODN to strengthen the activity and/or stability when the CpG-ODN is administered in vivo. In the MB-ODN of the present invention the preferred modification of the backbone includes modification into phosphorothioate, which is allowed to be resistant to its decomposition. The modification into phosphorothioate may be generated at the terminal ends, and for example two or three of the last 5' or 3' nucleotides may be connected by phosphorothioate bonds. Also, the MB-ODN of the present invention may be modified to have a secondary structure (for example, a stem-loop structure) so that it can be resistant to its decomposition. Preferably, the MB-ODN of the present invention may be modified to have a partially phosphorothioate-modified backbone. The phosphorothioate may be synthesized by the automatic techniques using phosphoramidate or H-phosphonate chemistry (S. E. Beaucage et al., *Tetrahe-* dron Lett., 22:1859, 1981: Froehler et al., Nucl. Acid. Res., 14:5399-5407). As another modification example, aryl- and alkyl-phosphonate may be synthesized, for example as described in U.S. Pat. No. 4,469,863, and alkylphosphotriester (a charged oxygen residue is alkylated, as described in U.S. Pat. No. 5,023,243 and EP Patent No. 092,574) may be manufactured by an automatic solid-phase synthesis using commercially available reagents. Also, still another modification example, which makes the MB-ODN less sensitive to the decomposition, includes acetyl-, thio- and similar modifications of adenosine, cytosine, guanine, thymine and uridine, as well as atypical bases such as inosine and quesine. The CpG-ODN having diols such as tetraethylglycol or hexaethyleneglycol at the terminal ends is also more resistant to its decomposition. In addition, the CpG-ODN further includes combination of phosphodiester and phosphorothioate, phosphotriester, phosphoramidate, methylphosphonate, methylphosphorothionate, phosphorodithoate and combinations thereof (Khorana et al., J. Molec. Biol., 72:209, 1972; Goodchild, J. Bioconjugate Chem., 4:165, 1990). As described above, the CpG-ODN having the modified backbone may have stronger immunological effects by means of enhanced nuclease resistance, increased cellular uptake, increased protein uptake and/or altered intracellular localization, etc.

The preferred backbone of the MB-ODN of the present invention is a phosphodiester (hereinafter, referred to as "O-type") or phosphorothioate (hereinafter, referred to as "S-type") backbone, and the most preferred backbone is the O-type backbone that is not easily decomposed in vivo to induce side effects.

It was seen that the MB-ODN according to the present invention strongly induces the humoral immune reactions by inducing expression of the Th1 cytokines, and has an adjuvant activity that improves efficiency of the vaccine. Specific physiological activities are as follows:

1) Production of IL-12 is increased in immune cells from a mouse and a mouse spleen.

2) Dendritic cells are activated to induce expression of the IL-12.

3) Production of antibodies is increased when HEL and the MB-ODN are used as an antigen and an adjuvant, respectively. At this time, it is revealed that production of IgG2a is more increased as a result of the Th1 immune reaction when CFA is used as an antigen.

The MB-ODN according to the present invention has an effect of improving the efficiency of the vaccine by means of the activities as described above. Unlike the conventional CpG-ODNs known in the prior art, the MB-ODN of the present invention is characterized in that it has nearly the same activity regardless of its backbone shapes. In the present invention, it was revealed that the CpG-ODN of the present invention modified into an O-type backbone has nearly the same activity as the CpG-ODN modified into an S-type backbone. Also, the CpG-ODN of the present invention may be effectively used as the adjuvant of the vaccine since it was revealed that it strongly induces the humoral immune reactions by inducing expression of the Th1 cytokines.

The MB-ODN according to the present invention has the physiological activities that control balance of the Th1/Th2 immune reaction by suppressing the Th2 cytokine (for example, IL-4), and/or inducing the Th1 cytokine (for example, IL-12). Specific physiological activities are as follows: 1) Macrophages are activated to activate an IL-12 promoter: 2) Dendritic cells are activated to induce expression of the IL-12; 3) Production of the IL-12 is increased in a mouse; 4) Production of the IL-12 is increased in immune cells of a mouse spleen; 5) Expression of cytokines (IL-4 and IL-10) mediated by Th2-lymphocytes is inhibited; 6) The cell number of CD4+ and CD8+ lymphocytes is reduced in a lesion site of the atopic dermatitis; and 7) A level of IgE is reduced in blood serum.

The MB-ODN according to the present invention has effects of treating the skin diseases or improving their symptoms by means of the activities as described above. Unlike the conventional CpG-ODNs known in the prior art, the CpG-ODN of the present invention is characterized in that it has nearly the same activity regardless of its backbone shape. In the present invention, it was revealed that the CpG-ODN of the present invention modified into an O-type backbone has nearly the same activity as, or the more excellent activity than the CpG-ODN modified into an S-type backbone. Therefore, the MB-ODN of the present invention may be useful to treat or prevent all the skin diseases. Also, the CpG-ODN of the present invention may be effectively used as a therapeutic agent of the immune-related diseases (for example, an asthma) that appear due to unbalance of the Th1/Th2 immune reaction since the balance of the Th1/Th2 immune reaction is maintained by inducing expression of the Th1 cytokines.

The MB-ODN according to the present invention has an effect of increasing viability of the immune cells. The MB-ODN has effects of stimulating macrophages to increase expression of Bcl-xs/L, and then inhibiting the apoptosis caused by the irradiation. Also, the MB-ODN has an effect of then inhibiting the apoptosis of the B cells caused by the irradiation. Accordingly, the MB-ODN may be effectively used to normalize the immune functions by increasing the viability of the normal immune cells when intractable diseases such as a cancer, etc. are treated using the irradiation. Specific physiological activities of the MB-ODN are as follows: 1) Expression of Bcl-xs/L is increased in the macrophages; 2) Viability of the macrophages is increased using the irradiation; and 3) Viability of the B cells is increased using the irradiation.

BRIEF DESCRIPTION OF THE DRAWINGS

These and other features, aspects, and advantages of preferred embodiments of the present invention will be more fully described in the following detailed description, taken accompanying drawings, incorporated herein in its entirety by this reference. In the drawings:

FIG. 1 is a result of analyzing chromosomal DNA sequences of *E. coli* and *M. bovis* BCG using a computer program. All DNA sequences (CpG motifs) in which two bases are present in both terminal ends of a CG dinucleotide are analyzed. As a result, it was confirmed that much more numbers of the CpG motifs are present in the chromosomal DNA of *M. bovis* BCG, as shown in FIG. 1.

FIG. 2 is a result of analyzing DNA sequences in which three CpG motifs are present on 20 base pairs among the DNA sequences present in the chromosomal DNA of *M. bovis* BCG. In the CpG motifs, the oligonucleotides have 4 and 5 base gaps between the bases C and C (-CGXXCGXXXCG-, MB-ODN 4/5; SEQ ID NO:16), and have each of 5 base gaps between the bases C and C (-CGXXXCGXXXCG-, MB-ODN 5/5; SEQ ID NO:45). It is shown that 395 oligonucleotides in the form of -CGXXCGXXXCG- (SEQ ID NO:16) and 354 oligonucleotides in the form of -CGXXXCGXXXCG- SEQ ID NO:45) are present in the chromosomal DNA of *M. bovis* BCG.

FIG. 3 is a table showing that 71 candidate oligonucleotides for controlling the immune reactions are selected and synthesized, and the used for detecting the candidate sequences.

FIG. 4a is a diagram showing a result of comparing how much 35 synthesized oligonucleotides in the MB-ODN 4/5 form activate an IL-8 promoter of the macrophage, FIG. 4b is a diagram showing a result of comparing how much 35 synthesized oligonucleotides in the MB-ODN 4/5 form activate an IL-12 promoter of the macrophage, and FIG. 4c is a diagram showing a result of comparing how much 35 synthesized oligonucleotides in the MB-ODN 5/5 form activate an IL-8 promoter of the macrophage.

FIG. 6 is a diagram showing a result of comparing how much the oligonucleotides MB-ODN 4/5#31 (M) in

EXAMPLE 1

Figure 4:
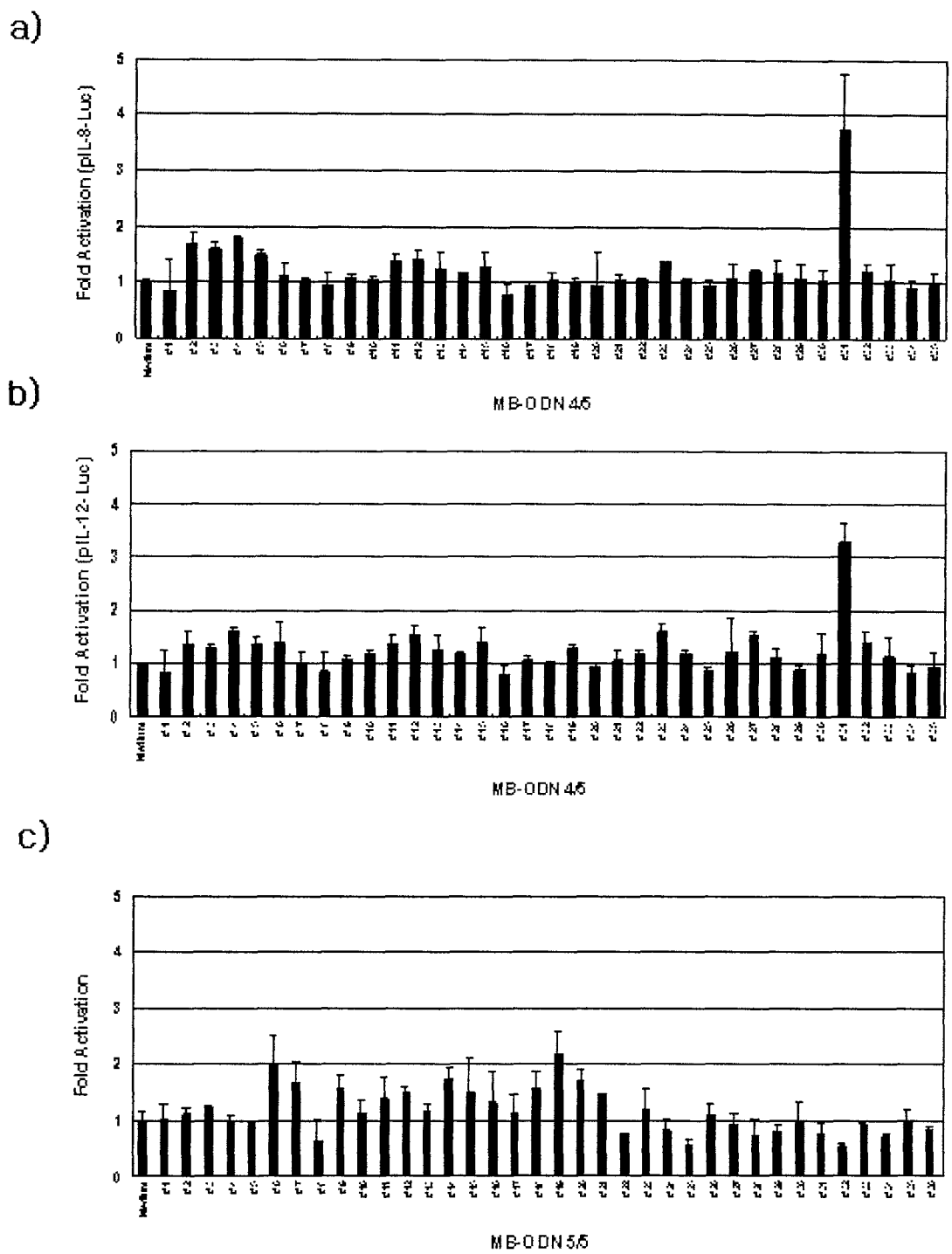
FIG. 4 is a diagram showing activation of IL-8 and IL-12 promoters in RAW 264.7 cells treated with the 71 oligonucleotides for controlling the immune reactions, synthesized in the form of the phosphodiester bond as shown in FIG. 3.
Figure 5:
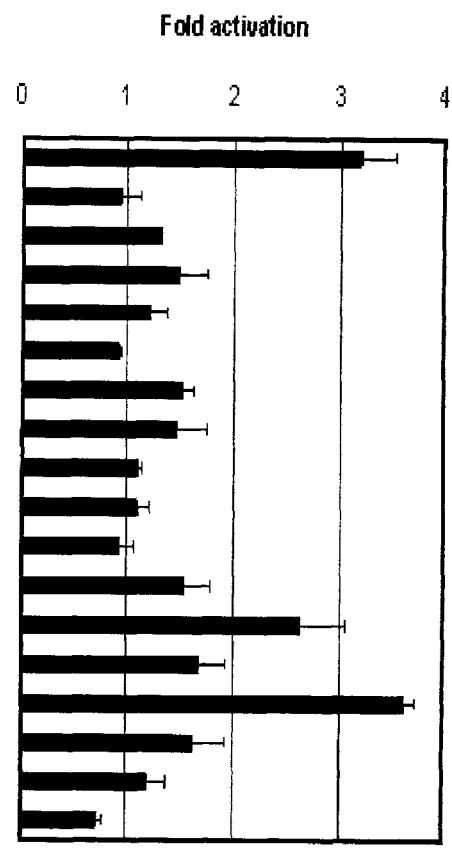
FIG. 5 is a diagram showing a result of selecting 17 oligonucleotides having five different DNA sequences toward each of 5' end and 3' end of the core CGTTCGTGTCG (SEQ ID NO:186) of MB-ODN 4/5#31 present on 20 base pairs among the DNA sequences present in the chromosomal DNA of *M. bovis* BCG (FIG. 5a), and then synthesizing the oligonucleotides with the phosphodiester backbones to compare how much the 17 oligonucleotides activate an IL-8 promoter of the macrophage (FIG. 5b).
Figure 7:
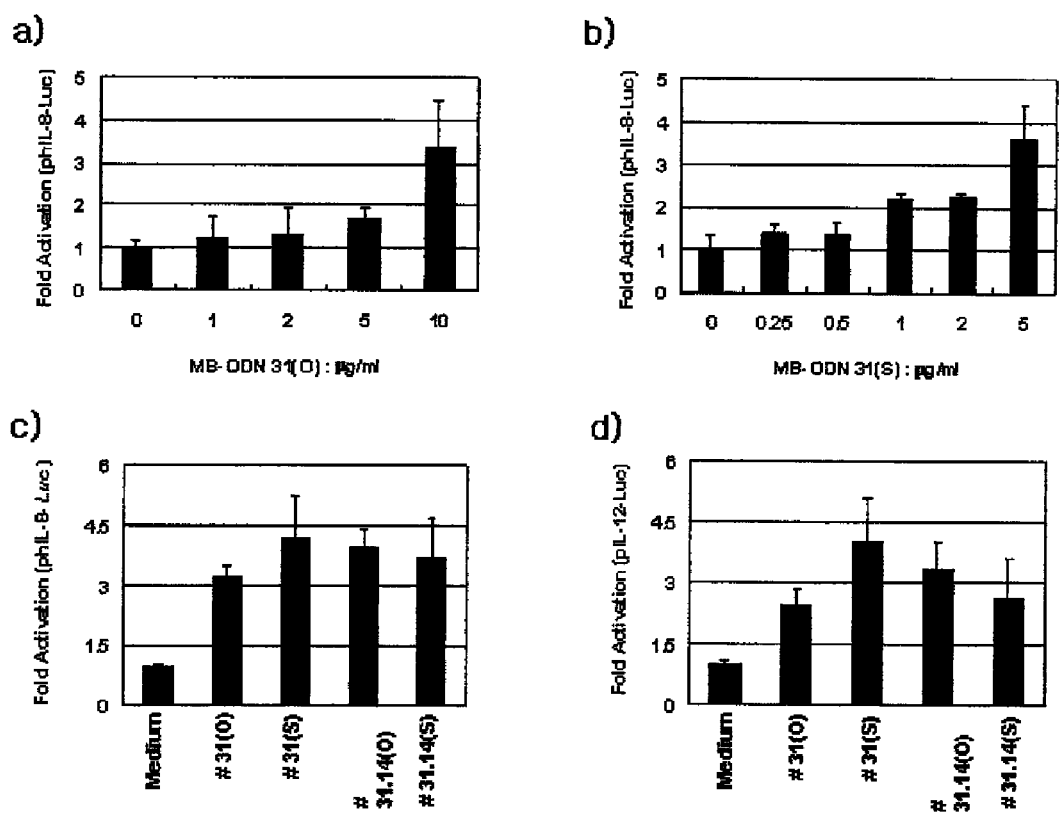

Analysis of DNA Sequences of Chromosomal DNAs from *E. coli* and *M. bovis* BCG

<1-1> Analysis of DNA Sequences of CpG Motifs in the Chromosomal DNAs from *E. coli* and *M. bovis* BCG The present inventors analyzed chromosomal DNA sequences of *E. coli* and *M. bovis* BCG using a computer program. The frequency of DNA sequences composed of 6 nucleotides, present in the chromosomal DNAs of *E. coli* and *M. bovis* BCG, was calculated using the computer program. It was found that the probability of the DNA sequence XXCGXX on the chromosomal DNA is theoretically $1/4^6$, but the probability of the sequence XXCGXX in the chromosomal DNAs of *E. coli* and *M. bovis* BCG is actually much higher. Also, it was confirmed that frequency of the sequence XXCGXX in the chromosomal DNA of *M. bovis*. BCG is more higher than that of *E. coli* (FIG. 1).

<1-2> Analysis of DNA Sequence of CpG ODN in Chromosomal DNA from *M. bovis* BCG 20 base pairs of Oligonucleotides were randomly selected from *M. bovis* BCG chromosomal DNA, and then the oligonucleotides including the three motifs XXCGXX were selected among them.

```
For example: GACGTTGAGTCGTTAACGAG    (SEQ ID NO: 187)
```

The results of analyzing the oligonucleotides having 4 and 5 base gaps between C and C (-CGXXCGXXXCG-, MB-ODN 4/5, FIG. 2a), and the oligonucleotides having each of 5 base gaps between C and C (-CGXXXCGXXXCG-, MB-ODN 5/5, FIG. 2b) SEQ ID NO:45) is listed, as shown in FIG. 2. It was shown that 395 oligonucleotides in the form of -CGXXCGXXXCG-(SEQ ID NO:16), and 354 oligonucleotides in the form of -CGXXXCGXXXCG- (SEQ ID NO:45) are present in the chromosomal DNA of *M. bovis* BCG. 20 base pairs of the oligonucleotides were listed on the order of priority by giving high marks to the oligonucleotides including the high frequencies of the motif XXCGXX, as shown in FIG. 1. The oligonucleotides whose CG is present in the 5'- or 3'-terminal end of 20 base pairs of the oligonucleotides was excluded, and then the 71 candidate oligonucleotides for controlling the immune reaction were selected, synthesized and used for detecting the candidate substances.

EXAMPLE 2

Detection of MB-ODN Having Immune Activity

<2-1> Immune Reaction of Synthesized Candidate MB-ODNs

It was examined whether or not the MB-ODNs prepared in the Example <1-2>, and their various substituents could activate the IL-8 and IL-12 promoters of the macrophages.

a) Cultivation of Mouse Macrophage

Raw 264.7 cells (ATCC, Manassas, Va.) were cultured in a DMEM medium including 10% FBS (Gibco BRL). Cell culture was carried out in a 5% $CO_2$ incubator (Form a) at 37° C.

b) Design of IL-8 and IL-12 Promoter-Luc Reporter Plasmid

In order to amplify an IL-8 promoter region (from −135 bp to +46 bp), human genome DNA was used as a template, and following primer sets were used to conduct a PCR reaction.

```
5' primer (SEQ ID NO: 9)   5'-GTGAGATCTGAAGTGTGATGACTCAGG-3'
3' primer (SEQ ID NO: 10)  5'-GTGAAGCTTGAAGCTTGTGTGCTCTGC-3'
```

A fragment of the amplified IL-8 promoter region was inserted into a pGL3-Basic plasmid (Promega) digested by the restriction enzymes BglII and HindIII. Therefore, an IL-8 promoter-Luc reporter plasmid was constructed (Wu G. D. et al., *J. Biol. Chem.*, 272:2396-2403, 1997).

Meanwhile, in order to amplify an IL-12 promoter region (from −373 bp to +52 bp), human genome DNA was used as a template, and following primer sets were used to conduct a PCR reaction.

```
5' primer (SEQ ID NO: 11)  5'-CATGAGCTCAGCCTCCCGTCTGACC-3'
3' primer (SEQ ID NO: 12)  5'-CTGGGCTCGAGGGAGAGTCCAATGG-3'
```

A fragment of the amplified IL-12 promoter region was inserted into a pGL3-Basic plasmid (Promega) digested by the restriction enzymes Sac 1 and Xho 1. Therefore, an IL-12 promoter-Luc reporter plasmid was constructed (Wu G. D. et al, *J. Biol. Chem.*, 272:2396-2403, 1997).

c) Analysis of Promoter Activation: Luciferase Activity Assay

RAW 264.7 cells (ATCC, Rockviller, MID) were divided into 12-well plates at a concentration of $5 \times 10^4$ cells/well and cultured at 37° C. for 24 hours in a 5% $CO_2$ incubator. The cells were co-transfected with the IL-8 promoter-Luc reporter plasmid or the IL-12 promoter-Luc reporter plasmid, which were constructed in the b), and a pRL-null plasmid (Promega). Then, the co-transfected cells were cultured at 37° C. for 24 hours in the 5% $CO_2$ incubator. Each well was treated with the MB-ODNs (10 μg/well) shown in the FIG. 3, and cultured at 37° C. for 6 hours or 12 hours in the 5% $CO_2$ incubator. At this time, the control group was treated with PBS. Then, PLB (passive lysis buffer) of a dual-luciferase reporter assay system (Promega) was added to each well at a concentration of 100 μl/well to homogenize the cells. The cell lysates was centrifuged, and the resultant supernatant (15 μl) was used to conduct a luciferase assay. The luciferase activity was measured using a TD-20/20 (Turner designs) luminometer. Each promoter activity by treatment of the MB-ODNs was measured as a relative activity of the control group. That is, if activity of the control group was set to '1', then activities of the experimental groups were presented as fold activation of the control group.

As a result, it was confirmed that the DNA sequence of the MB-ODN4/5#31 activates the IL-8 promoter, as shown in FIG. 4.

<2-2> Activation of IL-8 Promoter by Oligonucleotides Homologous to MB-ODN415#31

20 base pairs of oligonucleotides, present in the chromosomal DNA of *M. bovis* BCG and homologous to the MB-ODN4/5#31, were analyzed, the homologous oligonucleotides having different DNA sequences except that they have the sequence CGTTCGTGTCG (SEQ ID NO:186) within the DNA sequences of MB-ODN4/5#31 having the effect of the IL-8 promoter activation, as shown in the Example <2-1>. As a result, it was seen that 17 oligonucleotides homologous to the MB-ODN4/5#31 are present, as shown in FIG. 5*a*. And then, the same method as in the Example <2-1> was repeated to measure the IL-8 promoter activity.

Accordingly, it was revealed that the ability to activate the IL-8 promoter is varied depending on the DNA sequences, as shown in FIG. 5*b*. It was seen that the MB-ODN4/5#31.14 also has high activity, in addition to the MB-ODN4/5#31 according to the present invention.

EXAMPLE 3

Modification and Immune Reaction of the DNA Sequence of the Oligonucleotide MB-ODN4/5#31

<3-1> Modification of DNA Sequence of the Oligonucleotide MB-ODN4/5#31

The DNA sequence of the oligonucleotide MB-ODN4/5#31 was modified to synthesize DNA sequences, as described FIG. 6. Each CG sequence of the MB-ODN4/5#31 was changed to a GC sequence (#31-CG-1, #31-CG-2, #31-CG-3). Also, the first CG and the second CG were changed to a GC sequence (#31-CG-4), the second CG and the third CG were changed to a GC sequence (#31-CG-5), and the first CG and the third CG were changed to a GC sequence (#31-CG-5). Each base G of the CG sequences was changed to A, T and C, respectively, as shown in FIG. 6*a*. Also, the first and second CG was changed to the sequence CA, and the second and third CG was changed to the sequence CA, and the first and third CG was changed to the sequence CA.

<3-2> Measurement of Immune Reactions by Oligonucleotides Modified from the Oligonucleotide MB-ODN4/5#31

$5\times10^4$ cells/well of RAW 264.7 cells were spread on a 12-well plate, and incubated at 37° C. for 24 hours in a 5% $CO_2$ incubator. An IL-8 promoter reporter plasmid and a pRL-null plasmid were co-transfected, and then incubated at 37° C. for 24 hours in a 5% $CO_2$ incubator. Each well was treated with synthetic oligonucleotides at 10 ug/well, and incubated at 37° C. for 6 hours in a 5% $CO_2$ incubator. Then, the same method as in the Example <2-1> was repeated to measure the IL-8 promoter activities.

The luciferase assay was used for measuring how much the synthetic oligonucleotides having any modified DNA sequences activates the IL-8 promoter of the macrophage. As a result,the IL-8 promoter was highly activated by the oligonucleotides 5'-AGCAGCGTTCGTGTGCGCCT-3'(SEQ ID NO:169), 5'-AGCAGCGTTCATGTCGGCCT-3 '(SEQ ID NO:177) 5'-AGCAGCGTTCGTGTCCGCCT-3' (SEQ ID NO:182) (FIG. 6*b*). Other synthetic oligonucleotides showed lower IL-8 promoter activities than the control group. In the oligonucleotides that activate the IL-8 promoter, the IL-8 promoter activities were measured even by the oligonucleotide having the second CpG motif TTCGTG variant “TTCATG”, which is not the CpG motif. It was revealed that when the third CpG motif “GTCGGC” was modified, the sequences GTGCGC and GTCCGC reappearing in the CpG motif could activate the IL-8 promoter (FIG. 6).

EXAMPLE 4

Examination of Immune Reaction by Backbone Modifications of Oligonucleotides MB-ODN4/5#31 and MB-ODN415#31.14

<4-1> Activation of RAW 264.7 Cells by Backbone Modifications of MB-ODN4/5#31 and MB-ODN4/5#31.14

RAW 264.7 cells were co-transfected with IL-8-Luc promoter reporter vector or IL-12-Luc promoter reporter vector constructed in the step b) of the Example <2-1>, and pRL-null plasmid (Promega). The transfected cells were treated with the O-type (phosphodiester backbone) and S-type (phosphorothioate backbone) MB-ODN4/5#31 and MB-ODN4/5#31.14 (0 or 10 μg/ml), and incubated for 8 hours, respectively. Then, the same method as in the Example <2-1> was repeated to measure activities of the IL-8 promoter and the IL-12 promoter. As a result, the oligonucleotides MB-ODN4/5#31 and MB-ODN4/5#31.14 according to the present invention showed the highest activities regardless of the backbone shapes (both of O-type and S-type), as shown in FIG. 7.

<4-2> Activation of NF-κB by Backbone Modifications of MB-ODN4/5#31 and MB-ODN4/5#31.14

A cover glass was put on a 24-well plate, and then RAM 264.7 cells was added at a concentration of $5\times10^5$ cells/ml and incubated at 37° C. for 24 hours in a 5% $CO_2$ incubator. Each well was treated with the oligonucleotides MB-ODN4/5#31 and MB-ODN4/5#31.14 at a quantity of 5 ug/well. After 30 minutes, the cells were immobilized using 3.7% formaldehyde, and then permeabilized with PBS including 0.2% Triton-X 100. The cells were blocked for 30 minutes in a solution in which 1% donkey serum was added to PBS (PBST) including 0.2% Tween-20, and then 0.5 ul/well of mouse anti-p65 (titer 1:500) antibodies was added to PBST and kept at room temperature for 2 hours. After the cells were washed with PBST, they were treated with Donkey-anti-mouse-IgG-FITC (titer 1:250) antibodies for 2 hours. Mobilization of the NF-κB into nuclei was observed using a confocal microscopy (Lee, Y., et. al., (2002) *Blood* 99, 4307-4317).

FIG. 8*a* is a photograph showing that NF-κB was stained using an immunostaining method and mobilization of the NF-κB into nuclei was observed using the confocal microscopy. The NF-κB was present in cytoplasm in an untreated control group or a CpG motif-free control group (non-CpG-ODN 2041). When the macrophages were treated with the MB-ODN4/5#31 and the MB-ODN4/5#31.14, the NF-κB was mobilized into the nuclei. The oligonucleotides MB-ODN4/5#31 and MB-ODN4/5#31.14 according to the present invention were mobilized into the nuclei regardless of the backbone shapes (both of O-type and S-type).

FIG. 8*b* is an electrophoretic diagram showing that NF-κB is activated in RAW 264.7 cell lines treated with MB-ODN4/5#31 and MB-ODN4/5#31.14 using an electrophoretic mobility shift assay (EMSA). $5\times10^5$ cells/ml of RAW 264.7 cells were added to each 6-well plate, and incubated at 37° C. for 24 hours in a 5% $CO_2$ incubator. Each cell was treated with the oligonucleotides MB-ODN4/5#31 and MB-ODN4/5#31.14 at a quantity of 5 ug/well. After 30 minutes, the cells were reacted in a nuclear extraction buffer, and then centrifuged to obtain nucleoprotein, which was used for conducting the EMSA. The probe (5'-AGTTGAGGGGACTTTC-CCAGGC-3') (SEQ ID NO: 13), which has a NF-κB binding site, was labeled with $^{32}P$ for the EMSA. The $^{32}P$-labeled probe and 20 ug of the nucleoprotein were mixed in a buffer (10 mM HEPES, pH 7.9, 65 mM NaCl, 1 mM dithiothreitol, 0.2 mM EDTA, 0.02% NP-40, 50 mg/ml poly (dIdC):poly (dIdC) and 8% glycerol), and then reacted at room temperature for 30 minutes. The reaction solution was electrophoresed in a 4% polyacrylamide gel including 0.5×TBE (1×TBE is 89 mMTris borate and 1 mM EDTA, pH 8.0) and 2.5% glycerol. The probe 5'-AGTTGAGGGGACTTTC-CCAGGC-3' (SEQ ID NO: 13) (Santa Cruz Biotechnology, Inc., Santa Cruz, Calif.) was used as an NF-κB competitor, and the cells were pre-treated 50 times so as to conduct the EMSA. An NF-κB antibody supershift assay was conducted by reacting the pre-treated cells with 1 ug of NF-κB antibodies at 4° C. for 30 minutes, and then the EMSA was carried out. In FIG. 8, it was seen from the EMSA that the NF-κB was activated by the MB-ODN4/5#31 and the MB-ODN4/5#31.14 in the RAW 264.7 cells. It was confirmed from the EMSA that the MB-ODN4/5#31 and the MB-ODN4/5#31.14 according to the present invention activate the NF-κB regardless of the backbone shapes (both of O-type and S-type).

EXAMPLE 5

Induction of Humoral Immune Reaction by MB-ODN4/5#31

<5-1> Immunization

A mixture of hen egg lysozyme (HEL, 50 mg/head) and MB-ODN4/5#31 (100 ug/head) was administered intraperitoneally into four-week-old Balb/c mice. After one week, a mixture of HEL and MB-ODN4/5#31 was administered at the same quantities once again. After one week, blood was drawn using a heart punching procedure, centrifuged to obtain serum by precipitating globules. The ELISA was carried out to measure titers of anti-HEL antibodies (the total IgG, Ig G1, Ig G2a) from the resultant serum.

<5-2> ELISA

The resultant serum was diluted 1:10 using PBS/0.2% sodium azide, and stored at −20° C. HEL (10 ug/ml sodium bicarbonate buffer, pH 9.6) was added to a 96-well immunoplate (Nunc), and kept at 4° C. for 16 hours to immobilize the HEL in the plate bottom. The plate was washed with PBST (PBS/0.05% Tween 20), and 1% bovine serum albumin (BSA) was added so as to block the cells, and kept at room temperature for one hour. The serum was continuously diluted 1:3 with PBS, sequentially added to the plate, kept at 4° C. for 16 hours, and then washed with PBST. An alkaline phosphatase-conjugated detecting antibody was mixed with PBST, added to the plate, and then kept at room temperature form 2 hours. A 1:2,000 goat anti-mouse Ig (H+L) (Southern Biotechnology Associates) antibody was used to detect the total amount of Ig. 1-StepTM ABTS (PIERCE) was added for color fixation, and absorption was measured at 405 nm using an ELISA reader (Labsystems) (Chu, R. S., et. al., (1997) *J. Exp. Med.* 186, 1623-1631).

Figure 9:
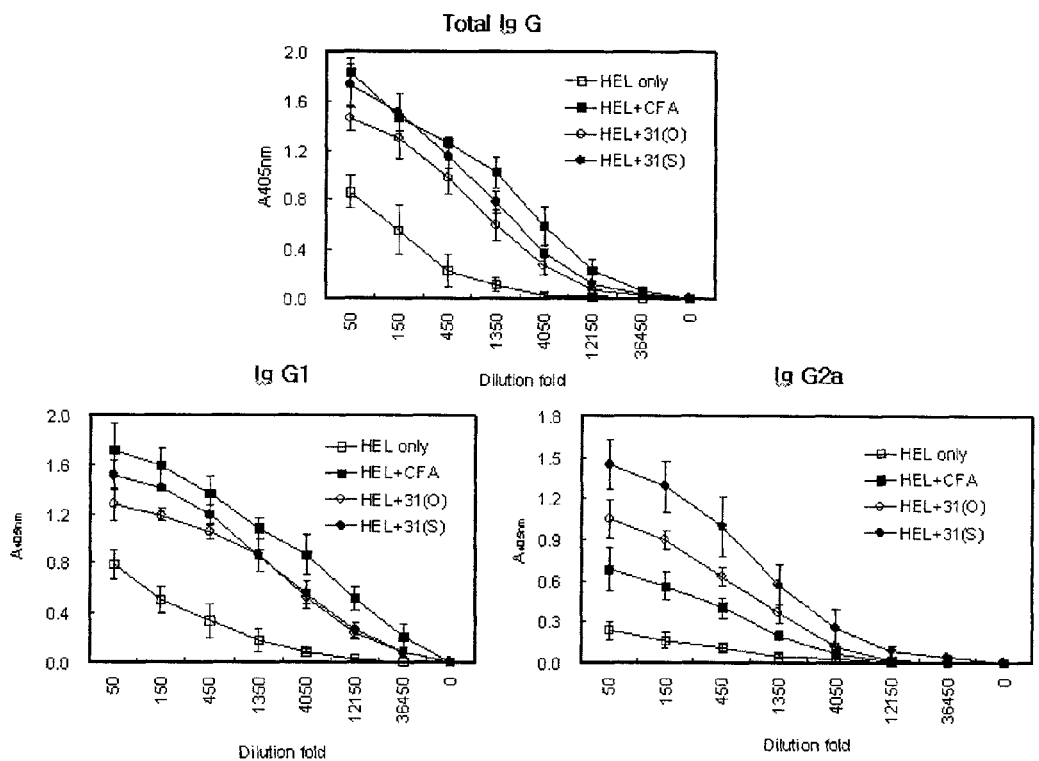

The MB-ODN4/5#31 was administered intraperitoneally into the Balb/c mice together with hen egg lysozyme (HEL) to examine a humoral immune reaction. It was confirmed that the MB-ODN4/5#31 segment has an adjuvant effect in the humoral immune reaction since the level of the antibody was more increased in the mice administered with HEL along with the MB-ODN4/5#31, compared to the mice administered with HEL alone (FIG. 9). Freund's adjuvant, which is a reagent manufactured by mixing an extract of *Mycobacteria* with paraffin oil, has been used as one of the representative adjuvants for about 60 years. However, the adjuvant has problems that it does not show a cell-mediated immunostimulatory effect and it should not be used in human. It was found that the MB-ODN4/5#31 could be used as a novel adjuvant since it acts as the adjuvant for stimulating the humoral immune reaction, and also stimulates the immune cells to induce the cell-mediated immune reaction. Also, it was shown that the MB-ODN4/5#31 was effectively used for producing the antibody of Th1 immune reaction-specific IgG2a.

EXAMPLE 6

Induced Production of Cytokines by MB-ODN4/5#31

<6-1> Expression of Cytokine in Dendritic Cell a) Separation of Dendritic Cell and its Treatment with MB-ODN4/5#31

Progenitor cell was isolated from bone marrow in the thigh of four-week-old Balb/c mice. The isolated progenitor cell was reacted with RBC lysis solution (150 mM $NH_4Cl$, 10 mM potassium carbonate, 0.1 mM EDTA, pH 7.4), and then harvested. The cell was divided into 6-well plates (Nunc) at a density of $2 \times 10^6$ cells/well. 10% FBS-containing RPMI medium, to which IL-4 and GM-CSF (Biosource) each were added, respectively, at a density of 10 ng/ml, was added to each well so as to differentiate the progenitor cell of bone marrow into dendritic cells (Ghosh, M., *J. Immunol.* 170: 5625-5629, 2003). The cells were incubated at 37° C. in a 5% $CO_2$ incubator. The cells were incubated for 6 days while changing the used medium with a fresh medium every 2 day. Then, the cells were treated with the O-type MB-ODN4/5#31, CpG-ODN 1826, and non-CpG-ODN 2041 according to the present invention at a level of 10 μg/ml.

b) Expression of IL-12 in Dendritic Cells

RT-PCR was carried out to measure an expression level of IL-12 in the dendritic cells treated with the O-type MB-ODN4/5#31 according to the present invention.

First, the dendritic cells separated from the Balb/c mouse in the Example <6-1a> were treated with O-type MB-ODN4/5#31 at a certain time (0, 0.5, 1, 2, 4 and 8 hours). The control groups were treated with O-type 1826 CpG ODN and 2041 non-CpG ODN, respectively.

Subsequently, the total RNA was isolated from the dendritic cells using TRIzol (Invitrogen). Then, the total RNA (5 μg) was treated with M-MLV reverse-transcriptase (Invitrogen) to construct cDNA. The resultant cDNA was used as the template, and a following specific primer set was used to carry out the PCR.

Forward primer (SEQ ID NO: 14)  5'-CTGGTGCAAAGAAACATGG-3'

Reverse primer (SEQ ID NO: 15)  5'-TGGTTTGATGATGTCCCTGA-3'

Figure 10:
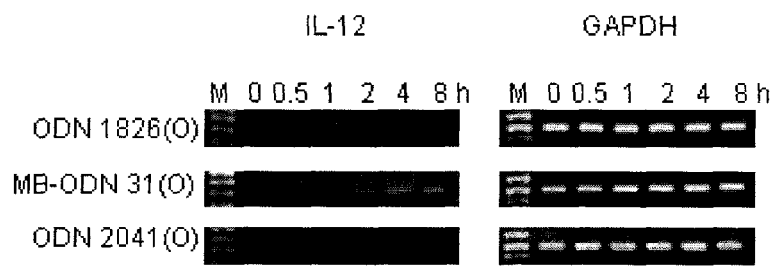

PCR amplification was carried out by repeating 25 cycles of DNA denaturation at 95° C. for 30 seconds; annealing of primers at 57° C. for 40 seconds and its extension at 72° C. for one minute. After the PCR amplification was completed, the amplified PCR product was confirmed in the 1% agarose gel. As a result, it was revealed that the expression of the IL-12 was induced only by the O-type MB-ODN4/5#31 of the present invention, as shown in FIG. 10. Meanwhile, the expression of the IL-12 was not induced by the S-type 1826 CpG ODN, in the contrary to the reports that the expression of the IL-12 was highly induced by the S-type 1826 CpG ODN (Lee, K W. et al., *Mol. Immunol.* 41:955-964, 2004).

<6-2> Expression of IL-12 by MB-ODN4/5#31 in Mouse

The ELISA was carried out after immunization so as to measure an expression level of IL-12p40 in the mouse treated with the MB-ODN4/5#31 according to the present invention.

a) Immunization

The O-type and S-type MB-ODN4/5#31 and non-CpG-ODN 2041 (100 ug/mouse) were administered intraperitoneally into four-week-old Balb/c mice, respectively. After 24 hours, blood was drawn using a heart punching procedure, centrifuged to obtain serum by precipitating globules.

b) ELISA

First, the ELISA was carried out to measure titers of the anti-IL-12p40 and anti-IL-4 antibodies in the serum isolated from the Balb/c mouse immunized with the MB-ODN4/5#31, as described in the Example <5-2>.

Figure 11:
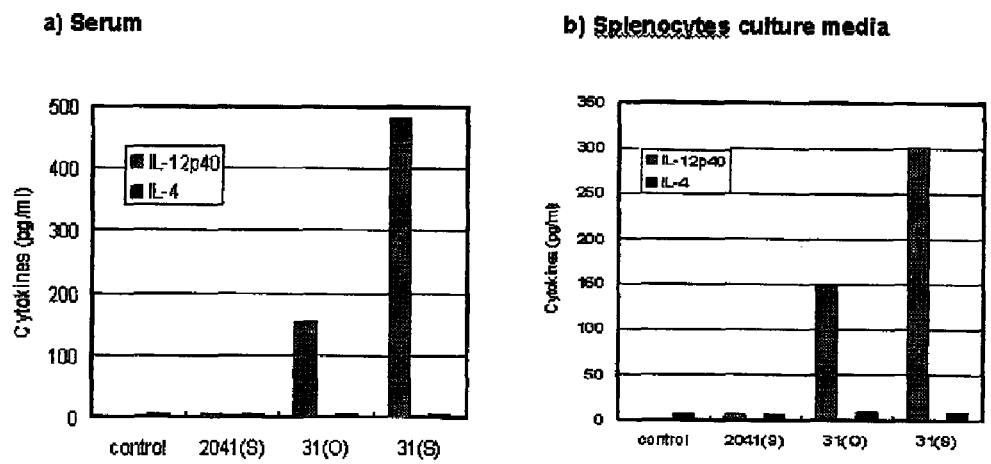

The MB-ODN4/5#31 was administered intraperitoneally into the Balb/c mice to compare the production levels of IL-12p40 and IL-4. As a result, the MB-ODN4/5#31 of the present invention induced production of the IL-12p40, but did not affect the production level of the IL-4, as shown in FIG. 11a. And, the S-type MB-ODN4/5#31 increased the production of the IL-12p40 to a higher level. Therefore, it was seen that the MB-ODN4/5#31 of the present invention has an effect of improving the Th1 immune reactivity by inducing the production of the IL-12p40.

<6-3> Expression of IL-12 by MB-ODN4/5#31 in Mouse Spleen Immune Cell

Immune cells were harvested from a spleen of the mouse, and divided into each well at a density of $5 \times 10^5$ cells/well. Then, each cell was treated with the O-type or S-type MB-ODN4/5#31 and non-CpG-ODN 2041 (0 or 10 μg/ml), and incubated for 24 hours. The cell culture was separated after the incubation was completed. In order to measure a level of the cytokine in the cell culture, a sandwich ELISA was then carried out using each of the commercially available anti-IL-12 p40 and IL-4 antibodies (R&D systems, Minneapolis, Minn.), as described in the Example <5-2>.

As a result, the MB-ODN4/5#31 of the present invention highly increased the expression level of the IL-12 p40 in the spleen immune cells regardless of the backbone shapes, as shown in FIG. 11b. But, the MB-ODN4/5#31 of the present invention did not affect the expression of the IL-4. Especially, the representative cytokine IL-12, which induces the Th1 immune reaction in the Th1/Th2 immune reaction, was induced by the MB-ODN4/5#31 of the present invention, and therefore it was confirmed that the MB-ODN4/5#31 of the present invention could induce the Th1 immune reaction.

EXAMPLE 7

In Vivo Analysis to Examine Ability to Treat Atopic Dermatitis

<7-1> Application of MB-ODN4/5#31-Containing Ointment of the Present Invention

6 NC/Nga mice were divided into two group: an MB-ODN4/5#31-treated group and an untreated group. The ointment (0.2 mg/head) including the resultant O-type MB-ODN4/5#31 was applied onto a lesion site of the atopic dermatitis in the back of the treated group of the mice every five days during 2 weeks (total 4 times). Petrolatum devoid of the CpG ODN of the present invention was applied to the untreated group of the mice in the same manner as described above.

<7-2> Observation of Lesion

Figure 12:
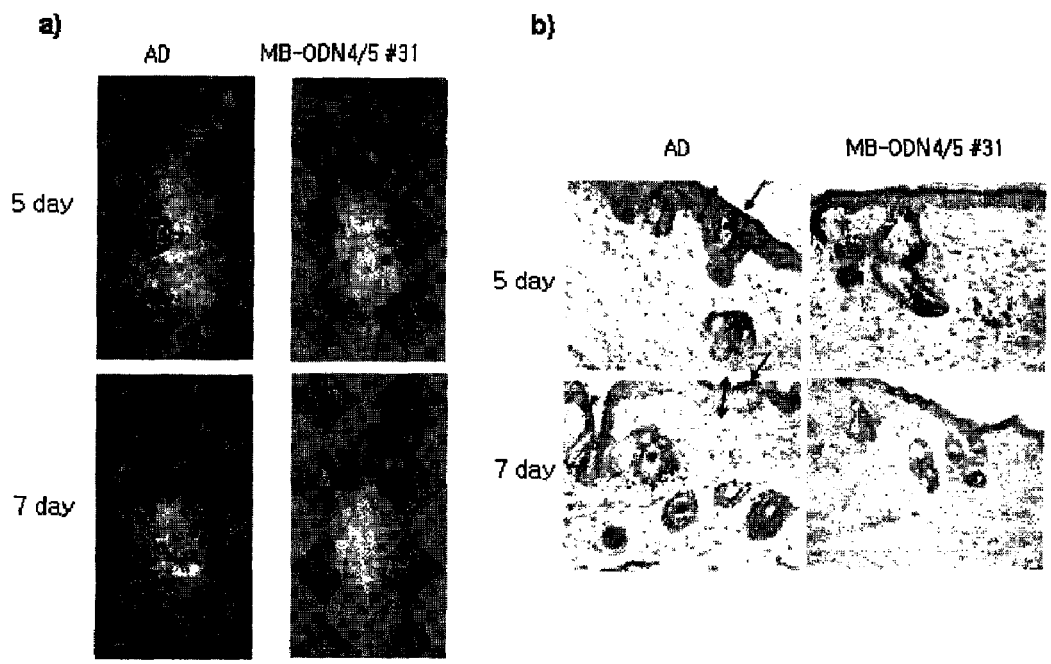

The lesion site of the atopic dermatitis was visually observed 5 or 7 days after application of the ointment including the MB-ODN4/5#31 of the present invention. As a result, disappearance of the skin lesions were observed in the back of the mice to which the O-type MB-ODN4/5#31 was applied, compared to the untreated group of the mice, as shown in FIG. 12a. Also, skins were taken from the back of the mice to examine an efficacy in treating the atopic dermatitis using H&E staining techniques. As a result, it was confirmed that hyperkeratosis and acanthosis were significantly reduced in the lesion site of the mice to which the O-type MB-ODN4/5#31 of the present invention was applied, and infiltration of lymphocytes in the dermis was also reduced, which shows that the atopic dermatitis was treated in the lesion site of the mice, as shown in FIG. 12b.

<7-3> Histological Analysis a) Expression of Cytokines $1.5 \times 1.5$ cm$^2$ of skins were taken 5, 7 and 14 days after application of the ointment including the MB-ODN4/5#31 of the present invention. Then, the skins were fixed in a 4% formalin solution for at least 1 day. The fixed skin tissues was treated with paraffin and cut at the thickness of 5 μm. After paraffin was removed, an experiment was carried out according to a manual of LSAB+kit (DAKO, Denmark), as follows. The resultant skin tissues was treated with 3% $H_2O_2$ for 10 minutes. Then, The skin tissues were blocked by adding 10% normal goat serum diluted with TBS (Tris-buffered saline, pH7.4) including 0.1% BSA. Then, the skin tissues were treated with primary antibodies such as a goat anti-mouse IL-10 antibody, a goat anti-mouse IL-4 antibody (Santa Cruz, USA), a rat anti-mouse IFN-antibody (Pierce, USA), and reacted at 4° C. for at least 12 hours. Then, the skin tissues were reacted with biotin-labeled secondary antibody at room temperature for at least 30 minutes, and then peroxidase-labeled streptavidin was added thereto and reacted at room temperature for about 30 minutes. A DAB Substrate chromogen system (DAKO, Denmark) was used to stain the skin tissues, and then the stained skin tissues were observed using a microscope.

Figure 13:
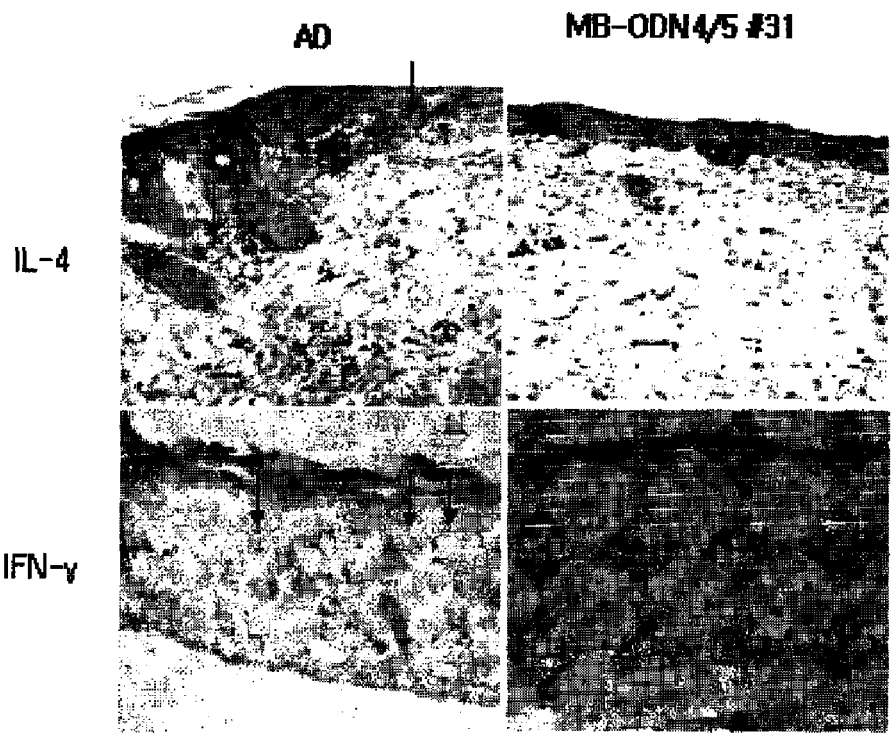

As a result, it was revealed that expression of the IL-4 was reduced, but expression of IFN-gamma was increased in the epidermis of the mice taken 5 days after application of the ointment including the MB-ODN4/5#31 of the present invention, as shown in FIG. 13. Therefore, it was seen that the O-type MB-ODN4/5#31 of the present invention suppresses production of the cytokine IL-4 mediated by Th2 phenotype T lymphocyte which is specifically high in the atopic dermatitis, while the O-type MB-ODN4/5#31 of the present invention improves and treats the conditions of the atopic dermatitis by increasing the production of the cytokine IFN-gamma mediated by Th1 phenotype T lymphocyte.

b) Measurement of Cell Numbers of CD4+ and CD8+ Lymphocytes $1.5 \times 1.5$ cm$^2$ of skins were taken 5, 7 and 14 days after application of the ointment including the O-type MB-ODN4/5#31 of the present invention. The obtained skin tissues were frozen with liquid nitrogen. Then, the skin tissues were inserted into a specimen block using a Tissue-Tek OCT compound (Sakura Finetek USA, INC.), and cut at the thickness of 5 μm using a cryostat. The cut skin tissues were reacted with the primary antibodies such as a rat anti-mouse CD4 mAb (BD phamingen, USA) or a rat anti-CD8 mAb (Serotec, UK) at 4° C. for 12 hours. Then, the resultant skin tissues were reacted with biotin-labeled secondary antibody at room temperature for at least 30 minutes, and then peroxidase-labeled streptavidin was added thereto and reacted at room temperature for about 30 minutes. A DAB Substrate chromogen system (DAKO, Denmark) was used to stain the skin tissues, and then the stained skin tissues were observed using a microscope. The photographs all were taken at 100 magnifications.

Figure 14:
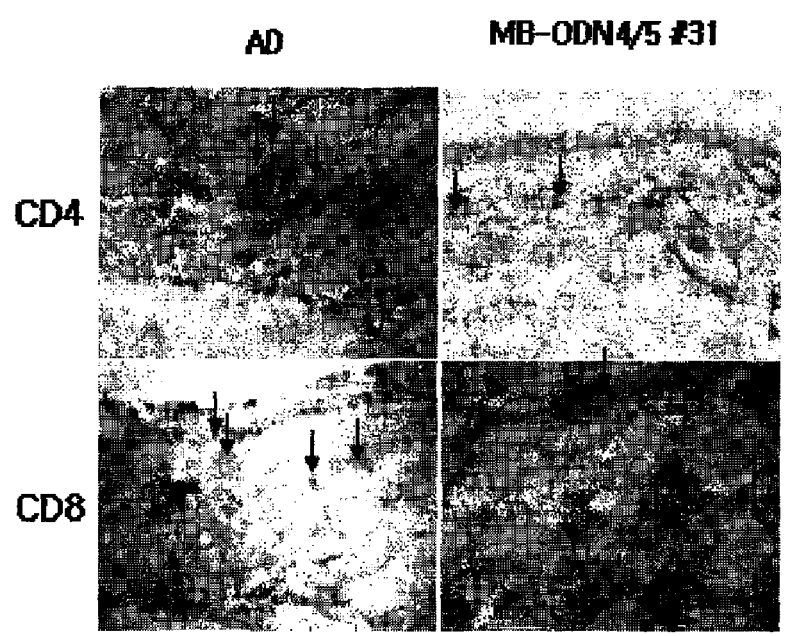

As a result, it was revealed that the CD4+ and CD8+ lymphocytes were reduced in the skins of the mice to which the O-type MB-ODN4/5#31 of the present invention was applied, as shown in FIG. 14. It was shown that reduction of the CD4+ and CD8+ lymphocytes in the lesion of the atopic dermatitis makes it very effective to treat the atopic dermatitis (Christian V., et al. *J Clin Invest.* 104:1097-1105, 1999).

<7-4> Analysis of IgE Level in Serum

Blood plasma was taken from each group of the mice, and stored at −20° C. until its use. The total IgE level was measured using a mouse IgE BD OptEIA Kit (BD Phamingen, USA). In order to examine a level of IgE antibody (BD Pharmingen, USA) in the plasma, a commercially available biotin-labeled IgE antibody (BD pharmingen, USA) was then used to carry out a sandwich ELISA, as described above in Example 5-2.

Figure 15:
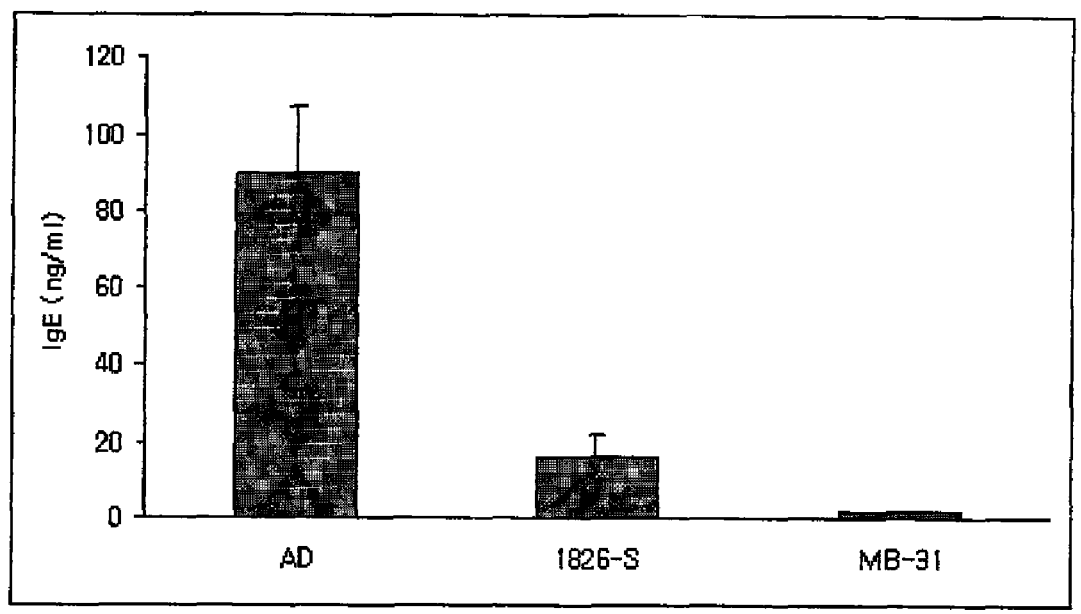

As a result, the IgE level in the serum was significantly reduced in the mice to which the ointment including the O-type MB-ODN4/5#31 of the present invention was applied, as shown in FIG. 15.

From the above result, it was seen that the O-type MB-ODN4/5#31 of the present invention increases expression of the cytokine mediated by Th1 lymphocyte, while the O-type MB-ODN4/5#31 of the present invention has a very excellent efficacy in treating the atopic dermatitis by suppressing expression of the cytokine mediated by Th2 lymphocyte to reduce the IgE level in the serum.

EXAMPLE 8

Effect of MB-ODN4/5#31 on Viability of Immune Cells by Irradiation

<8-1> Expression of Bcl-xs/L by Treatment of MB-ODN4/5#31

$1 \times 10^5$ cells/well of RAW 264.7 cells were spread on a 6-well plate, and incubated at 37° C. for 24 hours in a 5% $CO_2$ incubator. Each cell was treated with the synthetic oligonucleotides at a density of 10 ug/well, and incubated at 37° C. for 6 hours in a 5% $CO_2$ incubator. 100 ul/well of a lysis buffer was added to homogenate the RAW 264.7 cells. Cell lysate was centrifuged to obtain a supernatant (15 ul), which was used to conduct a Western blotting assay. The resultant supernatant was treated with the antibody-goat anti-mouse Bcl-xs/L, and reacted with the peroxidase-labeled secondary antibody, and then an enhanced chemiluminescence reagent (Amersham Pharmacia Biotech, Piscataway, N.J., USA) was used to observe the Bcl-xs/L.

Figure 16:
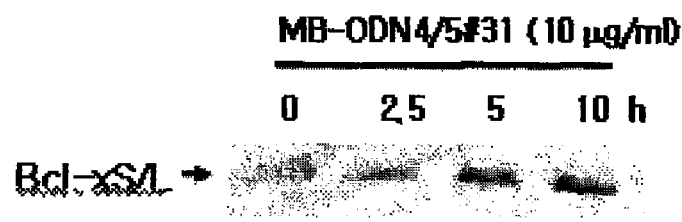

As a result, it was seen that the MB-ODN4/5#31 according to the present invention functions to increase viability of the cells by stimulating expression of the Bcl-xs/L, in the RAW264.7 cells, as shown in FIG. 16.

<8-2> Observation of Increased Viability of Macrophage by Treatment with MB-ODN4/5#31

$3 \times 10^4$ cells/well of RAW 264.7 cells were spread on a 4-well chamber slide (Lab-TEK Chamber slide, Nalge Nunc International, Inc), and incubated at 37° C. for 24 hours in a 5% $CO_2$ incubator. Each cell was treated with the synthetic oligonucleotides were treated at a density of 10 ug/well for 6 hours, irradiated with a 10 Gy γ-irradiator and then incubated at 37° C. for 48 hours in a 5% $CO_2$ incubator. A 3-(4,5-dimethylthiazole-2-yl)-2,5-diphenyl tetrazolium bromide (MTT) solution (5×, 2 ug/ml) was directly added to a medium of the incubated RAW 264.7 cells (to final concentration of 0.4 ug/ml), and reacted at 37° C. for 4 hours in a 5% $CO_2$ incubator. After the media were completely removed from each well, 0.5 ml of DMSO was added, and then reacted at 37° C. for 10 minutes to dissolve resultant formazan crystals. 100 ul of a reaction solution was taken and used to measure its absorption at 570 nm.

Figure 17:
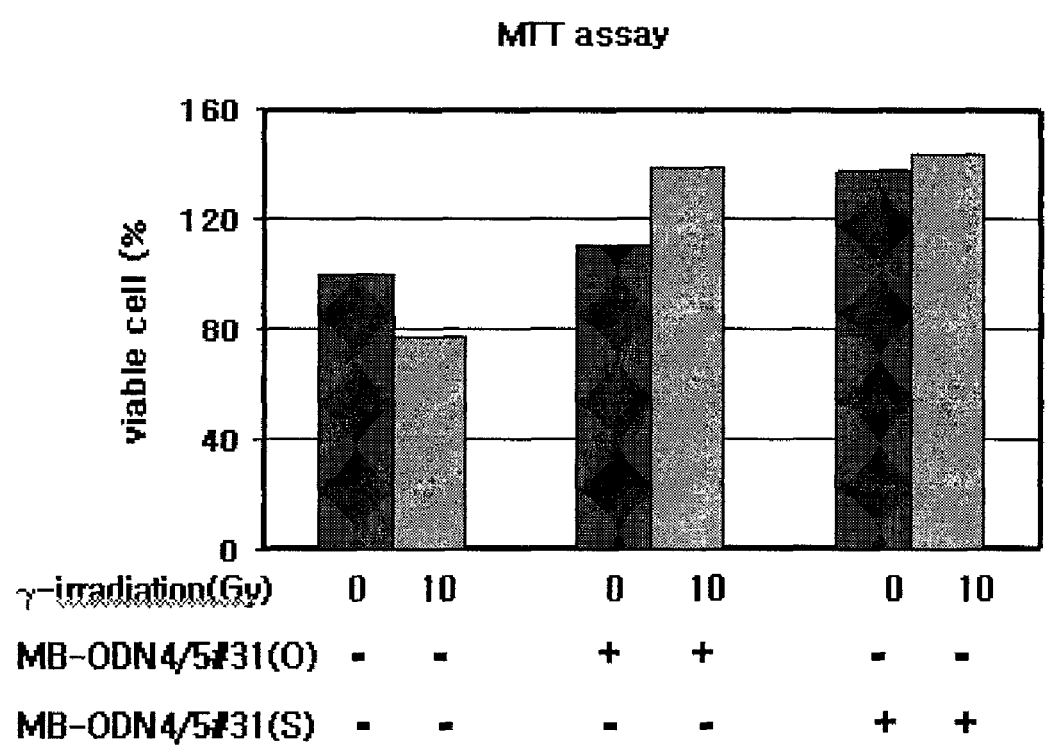

As a result, it was seen that treatment of the MB-ODN4/5#31 according to the present invention prevents the RAW 264.7 cells from being killed by irradiation, as shown in FIG. 17. For the backbone shapes, the O-type MB-ODN4/5#31 has the higher activity.

<8-3> Observation of Increased Viability of B Cells by Treatment with MB-ODN4/5#31

$1 \times 10^5$ cells/well of RPMI 8226 cells were spread on a 6-well plate, and treated with the synthetic oligonucleotides at a density of 10 ug/well for 6 hours, irradiated with a 10 Gy γ-irradiator, and then incubated at 37° C. for 48 hours in a 5% $CO_2$ incubator. 50 ug/ml of propidium iodide (PI) was added to the incubated cells, reacted in ice for 10 minutes, and then a level of the cell stained with PI was measured using a Flow Cytometry.

Also, the incubated cells were washed twice with cold PBS, and 5 ul of Annexin V-PE was added, and then reacted at room temperature for 15 minutes. 0.4 ml of an Annexin V binding buffer was added thereto to measure a level of the cells bound to Annexin V, using a Flow Cytometry.

Figure 18:
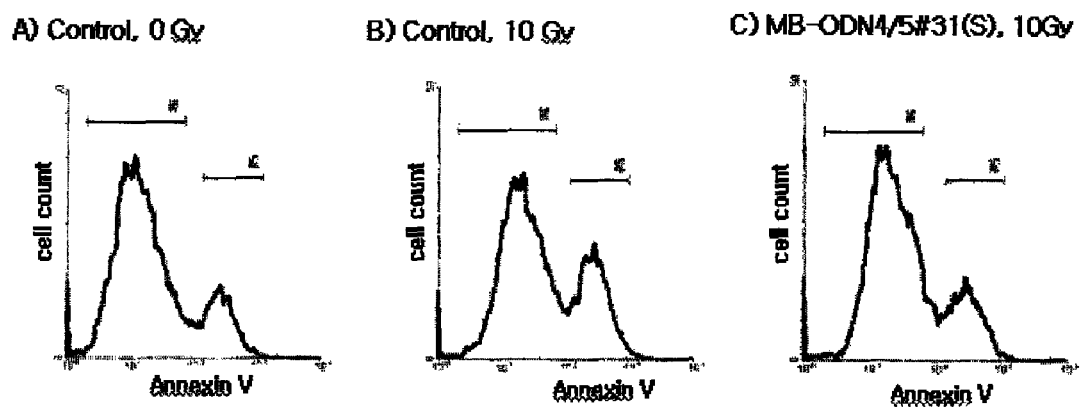
Figure 19:
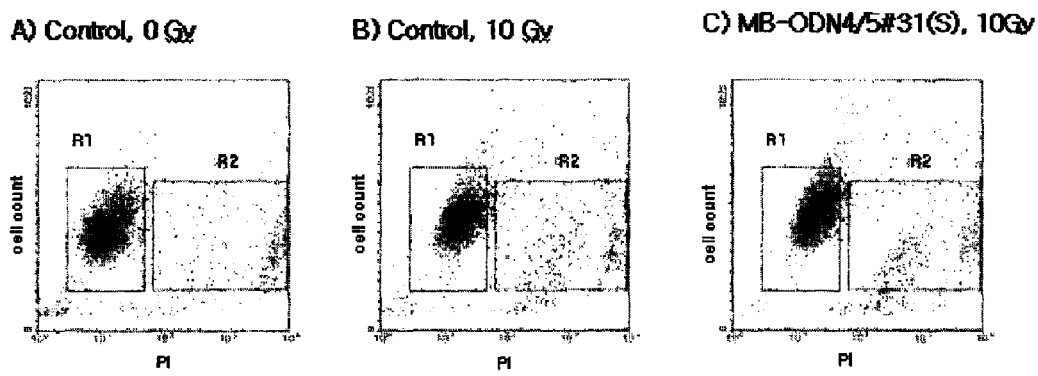

As a result, it was seen that treatment of the MB-ODN4/5#31 according to the present invention prevents the RPMI 8226 cells from being killed by irradiation, as shown in FIGS. 18 and 19.

From the results described above, it was confirmed that the MB-ODN4/5#31 of the present invention has the very excellent efficacy in normalizing the immune functions by increasing viability of the normal immune cells when the intractable diseases such as a cancer, etc. are treated by irradiation.

INDUSTRIAL APPLICABILITY

As described above, it was seen that *Mycobacterium bovis* BCG-derived oligonucleotide segments according to the present invention was involved in the humoral immune reaction by acting as the adjuvant to form the HEL antibody, and involved in the activation of the innate immune cells by activating the IL-8 promoter in the activation cascade of the IL-8 and IL-12 promoters of the macrophage. Also, it was confirmed that the oligonucleotides of the present invention might be used as a novel adjuvant since it acts as the adjuvant for stimulating the humoral immune reaction, and also stimulates the immune cells to induce the cell-mediated immune reaction. And it was revealed that the MB-ODN of the present invention increases expression of the cytokine mediated by Th1 lymphocyte in the NC/Nga mouse, which is an animal model for the atopic dermatitis, while the MB-ODN of the present invention has a very excellent efficacy in treating the atopic dermatitis by suppressing expression of the cytokine mediated by Th2 lymphocyte to reduce the IgE level in the serum.

Also, it was confirmed that the MB-ODN4/5#31 of the present invention has the very excellent efficacy in normalizing the immune functions by increasing viability of the normal immune cells when the intractable diseases such as a cancer, etc. are treated by irradiation.

What is claimed is:

1. An isolated oligonucleotide consisting of

HKCGTTCRTGTCSGM    (SEQ ID NO: 1)

wherein, R represents A or G; S represents C or G; H represents A, T or C; K represents G or T; and M represents C or A.

2. An isolated oligonucleotide consisting of

DKMHKCGTTCRTGTCSGMYK    (SEQ ID NO: 2)

wherein, R represents A or G; S represents C or G; H represents A, T or C; K represents G or T; D represents A, G or T; M represents C or A; M represents C or A; and Y represents C or T.

3. The oligonucleotide according to any one of claims 1 and 2, wherein the oligonucleotide has a phosphodiester bond or phosphorothioate bond between the nucleotides.

4. The oligonucleotide according to any one of claims 1 and 2, wherein the oligonucleotide is selected from the group consisting of 5'-AGCAGCGTTCGTGTCGGCCT-3' (SEQ ID NO: 3), 5'-AGCAGCGTTCGTGTGCGCCT-3' (SEQ ID NO: 4), 5'-AGCAGCGTTCATGTCGGCCT-3' (SEQ ID NO: 5), 5'-AGCAGCGTTCGTGTCCGCCT-3' (SEQ ID NO: 6), 5'-GTATTCGTTCGTGTCGTCCT-3' (SEQ ID NO: 7) and 5'-TGACTCGTTCGTGTCGCATG-3' (SEQ ID NO: 8).

5. The oligonucleotide of claim 1 wherein said oligonucleotide is an adjuvant.

6. The oligonucleotide of claim 2 wherein said oligonucleotide is an adjuvant.

7. A method for treating atopic dermatitis, comprising: administrating to a subject diagnosed with atopic dermatitis a composition comprising an isolated oligonucleotide consisting of the nucleic acid sequence set forth in SEQ ID NO: 3 under conditions such that symptoms of atopic dermatitis are reduced.

8. A method for increasing viability of normal immune cells when radiotherapy is applied, comprising: administrating to a subject undergoing radiotherapy in need thereof a composition comprising an isolated oligonucleotide consisting of the nucleic acid sequence set forth in SEQ ID NO: 3 under conditions such that viability of said subject's immune cells is increased in the presence of said oligonucleotide.

\* \* \* \* \*